(12) United States Patent
Wang et al.

(10) Patent No.: US 11,964,076 B2
(45) Date of Patent: Apr. 23, 2024

(54) MULTI-LAYERED POLYMER FILM FOR SUSTAINED RELEASE OF AGENTS

(71) Applicant: Foundry Therapeutics, Inc., Menlo Park, CA (US)

(72) Inventors: Honglei Wang, Singapore (SG); Jingnan Luo, Singapore (SG)

(73) Assignee: Foundry Therapeutics, Inc., Menlo Park, CA (US)

( * ) Notice: Subject to any disclaimer, the term of this patent is extended or adjusted under 35 U.S.C. 154(b) by 145 days.

(21) Appl. No.: 17/305,851

(22) Filed: Jul. 15, 2021

(65) Prior Publication Data

US 2022/0072207 A1 Mar. 10, 2022

Related U.S. Application Data

(63) Continuation of application No. 16/366,323, filed on Mar. 27, 2019, now abandoned, which is a continuation of application No. 15/563,527, filed as application No. PCT/SG2016/050158 on Mar. 31, 2016, now abandoned.

(30) Foreign Application Priority Data

Mar. 31, 2015 (GB) .................................. 1505527

(51) Int. Cl.
| | | |
|---|---|---|
| A61L 31/16 | (2006.01) | |
| A61K 31/496 | (2006.01) | |
| A61K 31/65 | (2006.01) | |
| A61L 27/54 | (2006.01) | |
| A61L 27/58 | (2006.01) | |
| A61L 31/04 | (2006.01) | |
| A61L 31/06 | (2006.01) | |
| A61L 31/14 | (2006.01) | |
| A61N 1/375 | (2006.01) | |
| A61P 31/00 | (2006.01) | |

(52) U.S. Cl.
CPC ............ *A61L 31/16* (2013.01); *A61K 31/496* (2013.01); *A61K 31/65* (2013.01); *A61L 27/54* (2013.01); *A61L 27/58* (2013.01); *A61L 31/041* (2013.01); *A61L 31/06* (2013.01); *A61L 31/148* (2013.01); *A61N 1/375* (2013.01); *A61P 31/00* (2018.01); *A61L 2300/404* (2013.01); *A61L 2300/406* (2013.01); *A61L 2300/602* (2013.01)

(58) Field of Classification Search
CPC ........ A61K 9/7007; A61L 31/16; A61L 27/54
See application file for complete search history.

(56) References Cited

U.S. PATENT DOCUMENTS

| | | |
|---|---|---|
| 4,601,893 A | 7/1986 | Cardinal |
| 4,666,704 A | 5/1987 | Shalati et al. |
| 4,919,939 A | 4/1990 | Baker |
| 5,227,165 A | 7/1993 | Domb et al. |
| 5,451,408 A | 9/1995 | Mezei et al. |
| 5,458,582 A | 10/1995 | Nakao |
| 5,540,912 A | 7/1996 | Roorda et al. |
| 5,618,563 A | 4/1997 | Berde et al. |
| 5,700,485 A | 12/1997 | Berde et al. |
| 5,747,060 A | 5/1998 | Sackler et al. |
| 5,807,306 A | 9/1998 | Shapland et al. |
| 5,919,473 A | 7/1999 | Elkhoury |
| 5,931,809 A | 8/1999 | Gruber et al. |
| 5,942,241 A | 8/1999 | Chasin et al. |
| 6,046,187 A | 4/2000 | Berde et al. |
| 6,149,937 A | 11/2000 | Camu et al. |
| 6,214,387 B1 | 4/2001 | Berde et al. |
| 6,248,345 B1 | 6/2001 | Goldenheim et al. |
| 6,326,020 B1 | 12/2001 | Kohane et al. |
| 6,451,335 B1 | 9/2002 | Goldenheim et al. |
| 6,699,908 B2 | 3/2004 | Sackler et al. |
| 6,913,760 B2 | 7/2005 | Carr et al. |
| 7,074,426 B2 | 7/2006 | Kochinke |
| 7,220,433 B2 | 5/2007 | Cui et al. |
| 7,723,291 B2 | 5/2010 | Beals et al. |
| 7,727,954 B2 | 6/2010 | McKay |

(Continued)

FOREIGN PATENT DOCUMENTS

| | | |
|---|---|---|
| AU | 2012201226 B2 | 8/2014 |
| AU | 2013200515 B2 | 1/2016 |

(Continued)

OTHER PUBLICATIONS

Chun, et al., "Gastrointestinal and Biliary Stents", Journal of Gastroenterology and Hepatology Foundation and Blackwell Publishing Asia Pty Ltd, vol. 25, 2010, pp. 234-243.

Goindi, et al., "Development of Novel Ionic Liquid-Based Microemulsion Formulation for Dermal Delivery of 5-Fluorouracil", AAPS PharmSciTech 2014 15(4):810-821 (Year: 2014).

Guo, et al., "A type of esophageal stent coating composed of one 5-fluorouracil-containing EVA layer and one drug-free protective layer: In vitro release, permeation and mechanical properties", Journal of Controlled Release 2007 118:318-324 (Year: 2007).

(Continued)

*Primary Examiner* — Michael B. Pallay
(74) *Attorney, Agent, or Firm* — Fortem IP LLP

(57) ABSTRACT

There is provided a controlled-release antibiotic socket for securely holding an implantable medical device that is made from: at least one film having at least one polymer layer, where the at least one film is formed into the socket; at least one antibiotic agent; and at least one opening in the socket, where the at least one polymer layer comprises a biodegradable elastomeric polymeric material; and the at least one antibiotic agent is dispersed within at least one of the at least one polymer layers and/or, when the film comprises at least two polymer layers, the at least one antibiotic agent is disposed as a separate layer between two polymer layers. Also disclosed is the film used to make the socket and uses of both the socket and film.

20 Claims, 5 Drawing Sheets

(56) References Cited

U.S. PATENT DOCUMENTS

| | | |
|---|---|---|
| 7,741,273 B2 | 6/2010 | McKay |
| 7,824,703 B2 | 11/2010 | Scifert et al. |
| 7,947,301 B2 | 5/2011 | Bischoff et al. |
| 7,993,390 B2 | 8/2011 | Miller et al. |
| 8,067,026 B2 | 11/2011 | Ranade et al. |
| 8,080,059 B2 | 12/2011 | Fell |
| 8,153,149 B2 | 4/2012 | Verity |
| 8,202,531 B2 | 6/2012 | McKay |
| 8,221,358 B2 | 7/2012 | McKay |
| 8,231,891 B2 | 7/2012 | King |
| 8,246,571 B2 | 8/2012 | Simonton et al. |
| 8,257,393 B2 | 9/2012 | Cichocki |
| 8,357,388 B2 | 1/2013 | McKay |
| 8,420,600 B2 | 4/2013 | Burch et al. |
| 8,430,852 B2 | 4/2013 | Bischoff et al. |
| 8,470,360 B2 | 6/2013 | McKay |
| 8,523,569 B2 | 9/2013 | Neshat |
| 8,524,267 B2 | 9/2013 | Zanella et al. |
| 8,575,092 B2 | 11/2013 | Domb |
| 8,591,531 B2 | 11/2013 | Buevich et al. |
| 8,603,528 B2 | 12/2013 | Kronenthal |
| 8,623,396 B2 | 1/2014 | Gray et al. |
| 8,629,172 B2 | 1/2014 | McKay et al. |
| 8,632,839 B2 | 1/2014 | Stopek et al. |
| 8,652,504 B2 | 2/2014 | Li et al. |
| 8,652,525 B2 | 2/2014 | Moses et al. |
| 8,663,192 B2 | 3/2014 | Hester et al. |
| 8,697,117 B2 | 4/2014 | Zilberman |
| 8,703,119 B2 | 4/2014 | Yankelson et al. |
| 8,708,966 B2 | 4/2014 | Allen et al. |
| 8,715,223 B2 | 5/2014 | McKay |
| 8,728,493 B2 | 5/2014 | Burton et al. |
| 8,728,509 B2 | 5/2014 | McKay |
| 8,750,983 B2 | 6/2014 | Bonutti |
| 8,758,798 B2 | 6/2014 | Stopek et al. |
| 8,795,713 B2 | 8/2014 | Makower et al. |
| 8,809,530 B1 | 8/2014 | Wu et al. |
| 8,822,492 B2 | 9/2014 | Schachter |
| 8,846,068 B2 | 9/2014 | Wohabrebbi et al. |
| 8,865,205 B2 | 10/2014 | Shalaby |
| 8,877,226 B2 | 11/2014 | Zanella et al. |
| 8,889,173 B2 | 11/2014 | Zanella et al. |
| 8,900,620 B2 | 12/2014 | Fulmer et al. |
| 8,911,765 B2 | 12/2014 | Moses et al. |
| 8,920,867 B2 | 12/2014 | Stopek et al. |
| 8,951,552 B2 | 2/2015 | Shalaby et al. |
| 8,956,642 B2 | 2/2015 | Hobot et al. |
| 8,968,767 B2 | 3/2015 | McKay |
| 8,969,397 B2 | 3/2015 | Burright et al. |
| 8,980,317 B2 | 3/2015 | King |
| 8,999,368 B2 | 4/2015 | McDonald et al. |
| 9,005,634 B2 | 4/2015 | McDonald et al. |
| 9,011,965 B2 | 4/2015 | Gan et al. |
| 9,023,114 B2 | 5/2015 | Buevich et al. |
| 9,125,814 B2 | 9/2015 | He et al. |
| 9,125,917 B2 | 9/2015 | McKay et al. |
| 9,132,087 B2 | 9/2015 | Lichter et al. |
| 9,132,194 B2 | 9/2015 | McKay |
| 9,155,707 B2 | 10/2015 | Ying et al. |
| 9,161,903 B2 | 10/2015 | Drapeau et al. |
| 9,173,732 B2 | 11/2015 | Langer et al. |
| 9,198,758 B2 | 12/2015 | McKay |
| 9,205,052 B2 | 12/2015 | Kim et al. |
| 9,211,285 B2 | 12/2015 | McKay et al. |
| 9,265,733 B2 | 2/2016 | McKay |
| 9,283,283 B2 | 3/2016 | Giammona et al. |
| 9,289,409 B2 | 3/2016 | Zanella et al. |
| 9,295,462 B2 | 3/2016 | Choy et al. |
| 9,302,903 B2 | 4/2016 | Park et al. |
| 9,320,708 B2 | 4/2016 | Scifert et al. |
| 9,351,924 B2 | 5/2016 | Cho et al. |
| 9,352,137 B2 | 5/2016 | Simonton et al. |
| 9,358,223 B2 | 6/2016 | King |
| 9,375,420 B2 | 6/2016 | King |
| 9,402,918 B2 | 8/2016 | Koyakutty et al. |
| 9,402,973 B2 | 8/2016 | Phillips et al. |
| 9,457,176 B2 | 10/2016 | Lee et al. |
| 9,504,749 B2 | 11/2016 | McKay |
| 9,522,113 B2 | 12/2016 | Spada et al. |
| 9,549,920 B2 | 1/2017 | Wohabrebbi et al. |
| 9,566,241 B2 | 2/2017 | Ravis et al. |
| 9,597,132 B2 | 3/2017 | Houff |
| 9,610,194 B2 | 4/2017 | De Juan et al. |
| 9,610,243 B2 | 4/2017 | Clay et al. |
| 9,623,222 B2 | 4/2017 | McKay |
| 9,629,818 B2 | 4/2017 | Nadkarni et al. |
| 9,655,994 B2 | 5/2017 | McKay |
| 9,668,974 B2 | 6/2017 | Amselem et al. |
| 9,669,117 B2 | 6/2017 | Campbell et al. |
| 9,694,079 B2 | 7/2017 | Ottoboni et al. |
| 9,700,567 B2 | 7/2017 | Zanella et al. |
| 9,724,300 B2 | 8/2017 | Yamashita et al. |
| 9,764,066 B2 | 9/2017 | Sim et al. |
| 9,821,091 B2 | 11/2017 | Hossainy et al. |
| 9,833,548 B2 | 12/2017 | McKay et al. |
| 9,861,590 B2 | 1/2018 | Stopek et al. |
| 9,987,233 B2 | 6/2018 | Helliwell et al. |
| 11,202,754 B2 | 12/2021 | Naga et al. |
| 11,224,570 B2 | 1/2022 | Naga et al. |
| 2001/0044651 A1 | 11/2001 | Steinke et al. |
| 2001/0055607 A1 | 12/2001 | Levin |
| 2002/0106410 A1 | 8/2002 | Masters |
| 2003/0022876 A1 | 1/2003 | Ashton et al. |
| 2003/0036803 A1 | 2/2003 | McGhan |
| 2003/0118649 A1 | 6/2003 | Gao et al. |
| 2003/0152637 A1 | 8/2003 | Chasin et al. |
| 2003/0157162 A1 | 8/2003 | Krugner-Higby et al. |
| 2003/0190341 A1 | 10/2003 | Shalaby et al. |
| 2003/0215496 A1* | 11/2003 | Patel ............ A61K 9/4858 424/452 |
| 2004/0109893 A1 | 6/2004 | Chen et al. |
| 2004/0249441 A1 | 12/2004 | Miller et al. |
| 2005/0019404 A1 | 1/2005 | Sung et al. |
| 2005/0048115 A1 | 3/2005 | Mangena et al. |
| 2005/0152957 A1 | 7/2005 | Cleary et al. |
| 2005/0158382 A1 | 7/2005 | Cruz et al. |
| 2005/0206048 A1 | 9/2005 | Ryu et al. |
| 2006/0034887 A1 | 2/2006 | Pelissier |
| 2006/0079558 A1 | 4/2006 | Aberg et al. |
| 2006/0079559 A1 | 4/2006 | Aberg et al. |
| 2006/0269475 A1 | 11/2006 | Ryu et al. |
| 2007/0071790 A1 | 3/2007 | Ameer et al. |
| 2007/0134292 A1 | 6/2007 | Suokas et al. |
| 2007/0173787 A1 | 7/2007 | Huang et al. |
| 2007/0178138 A1 | 8/2007 | Pal et al. |
| 2007/0258939 A1 | 11/2007 | Lewis et al. |
| 2008/0089923 A1 | 4/2008 | Burkstrand et al. |
| 2008/0095849 A1 | 4/2008 | Wu et al. |
| 2008/0132922 A1 | 6/2008 | Buevich et al. |
| 2008/0154241 A1 | 6/2008 | Burkstrand et al. |
| 2008/0228193 A1 | 9/2008 | Matityahu |
| 2008/0241212 A1 | 10/2008 | Moses et al. |
| 2008/0311191 A1 | 12/2008 | Nangia et al. |
| 2009/0076595 A1 | 3/2009 | Lindquist et al. |
| 2009/0087380 A1 | 4/2009 | Fasching et al. |
| 2009/0123508 A1 | 5/2009 | Cheng et al. |
| 2009/0142400 A1 | 6/2009 | Hiles et al. |
| 2009/0155326 A1 | 6/2009 | Mack et al. |
| 2009/0177229 A1 | 7/2009 | Gulotta et al. |
| 2009/0182425 A1 | 7/2009 | Duda et al. |
| 2009/0198197 A1 | 8/2009 | Bischoff et al. |
| 2009/0263321 A1 | 10/2009 | McDonald et al. |
| 2009/0263441 A1 | 10/2009 | McKay |
| 2009/0263443 A1 | 10/2009 | King |
| 2009/0263451 A1 | 10/2009 | King |
| 2009/0264472 A1 | 10/2009 | Wohabrebbi et al. |
| 2009/0264477 A1 | 10/2009 | Zanella et al. |
| 2009/0264489 A1 | 10/2009 | Hildebrand et al. |
| 2009/0325879 A1 | 12/2009 | Norton et al. |
| 2010/0055437 A1 | 3/2010 | Fink et al. |
| 2010/0168808 A1 | 7/2010 | Citron |
| 2010/0198278 A1 | 8/2010 | Cobian et al. |
| 2010/0203100 A1 | 8/2010 | Cobian et al. |
| 2010/0203102 A1 | 8/2010 | Wohabrebbi |

(56) References Cited

U.S. PATENT DOCUMENTS

| | | |
|---|---|---|
| 2010/0249783 A1 | 9/2010 | Trieu |
| 2011/0027331 A1 | 2/2011 | Hobot |
| 2011/0060309 A1 | 3/2011 | Lee et al. |
| 2011/0081422 A1 | 4/2011 | Masinde et al. |
| 2011/0082545 A1 | 4/2011 | Freund |
| 2011/0129801 A1 | 6/2011 | Barman |
| 2011/0137243 A1 | 6/2011 | Hossainy et al. |
| 2011/0152839 A1 | 6/2011 | Cima et al. |
| 2011/0184037 A1 | 7/2011 | Haddock et al. |
| 2011/0206752 A1 | 8/2011 | Carreno et al. |
| 2011/0224245 A1 | 9/2011 | Schachter |
| 2011/0281882 A1 | 11/2011 | Zhang et al. |
| 2012/0009240 A1 | 1/2012 | Stopek et al. |
| 2012/0097194 A1 | 4/2012 | McDaniel et al. |
| 2012/0100192 A1* | 4/2012 | Penhasi ............ A61K 9/7007 514/570 |
| 2012/0114740 A1 | 5/2012 | Garcia et al. |
| 2012/0165795 A1 | 6/2012 | Seiler et al. |
| 2012/0239001 A1 | 9/2012 | Barry et al. |
| 2012/0263761 A1 | 10/2012 | McDonald et al. |
| 2012/0316199 A1 | 12/2012 | Ward et al. |
| 2013/0018321 A1 | 1/2013 | McKay |
| 2013/0071463 A1 | 3/2013 | Palasis et al. |
| 2013/0136811 A1 | 5/2013 | Schachter |
| 2013/0158652 A1 | 6/2013 | Palasis et al. |
| 2013/0164347 A1 | 6/2013 | Gensini et al. |
| 2013/0261594 A1 | 10/2013 | Stopek et al. |
| 2013/0280272 A1 | 10/2013 | Trogden et al. |
| 2014/0052183 A1 | 2/2014 | Freese |
| 2014/0065202 A1 | 3/2014 | Ito |
| 2014/0072608 A1 | 3/2014 | Logothetidis et al. |
| 2014/0086971 A1 | 3/2014 | Hall et al. |
| 2014/0088347 A1 | 3/2014 | Frigstad et al. |
| 2014/0105956 A1 | 4/2014 | Banerjee et al. |
| 2014/0107159 A1 | 4/2014 | Ebersole et al. |
| 2014/0170204 A1 | 6/2014 | Desai et al. |
| 2014/0193466 A1 | 7/2014 | Lawrence et al. |
| 2014/0193504 A1 | 7/2014 | Wooley et al. |
| 2014/0214175 A1 | 7/2014 | Barron et al. |
| 2014/0255464 A1 | 9/2014 | Hakimimehr et al. |
| 2014/0271770 A1 | 9/2014 | Clay et al. |
| 2014/0287053 A1 | 9/2014 | Helliwell et al. |
| 2015/0018969 A1 | 1/2015 | Fulmer et al. |
| 2015/0024031 A1 | 1/2015 | Rabinow et al. |
| 2015/0024116 A1 | 1/2015 | Matson et al. |
| 2015/0038415 A1 | 2/2015 | Zupancich |
| 2015/0039097 A1 | 2/2015 | Biris |
| 2015/0150988 A1 | 6/2015 | Shalaby et al. |
| 2015/0246001 A1 | 9/2015 | Zupancich et al. |
| 2015/0272877 A1 | 10/2015 | Shi et al. |
| 2015/0290170 A1 | 10/2015 | Liu et al. |
| 2015/0342964 A1 | 12/2015 | Gray et al. |
| 2016/0038632 A1 | 2/2016 | Shah et al. |
| 2016/0089335 A1 | 3/2016 | Ohri et al. |
| 2016/0136094 A1 | 5/2016 | Criscione et al. |
| 2016/0144040 A1 | 5/2016 | Cheng |
| 2016/0144067 A1* | 5/2016 | Armbruster ........ A61K 9/7007 606/71 |
| 2016/0184340 A1 | 6/2016 | Kritikou |
| 2016/0287367 A1 | 10/2016 | Rontal |
| 2016/0331853 A1 | 11/2016 | Taub |
| 2016/0339152 A1 | 11/2016 | Bonutti et al. |
| 2016/0354309 A1 | 12/2016 | Heitzmann et al. |
| 2017/0014337 A1 | 1/2017 | Walsh |
| 2017/0079929 A1 | 3/2017 | Davey |
| 2017/0128632 A1 | 5/2017 | McJames |
| 2017/0182168 A1 | 6/2017 | Ottoboni et al. |
| 2017/0196499 A1 | 7/2017 | Hunter |
| 2017/0196508 A1 | 7/2017 | Hunter |
| 2017/0216597 A1 | 8/2017 | Hou et al. |
| 2017/0239183 A1 | 8/2017 | Reynolds et al. |
| 2017/0246117 A1 | 8/2017 | Helliwell et al. |
| 2017/0281778 A1 | 10/2017 | Ottoboni et al. |
| 2018/0092855 A1 | 4/2018 | Kim et al. |
| 2019/0351108 A1 | 11/2019 | Wang et al. |
| 2020/0009293 A1 | 1/2020 | Teu et al. |
| 2020/0246255 A1 | 8/2020 | Naga et al. |
| 2020/0368398 A1 | 11/2020 | Naga et al. |
| 2021/0186868 A1 | 6/2021 | Naga et al. |
| 2021/0308338 A1 | 10/2021 | Ruane et al. |
| 2021/0361827 A1 | 11/2021 | Teu et al. |
| 2022/0117885 A1 | 4/2022 | Naga et al. |
| 2022/0183963 A1 | 6/2022 | Kim et al. |
| 2022/0183964 A1 | 6/2022 | Naga et al. |

FOREIGN PATENT DOCUMENTS

| | | |
|---|---|---|
| CN | 1344156 A | 4/2002 |
| CN | 1655738 A | 8/2005 |
| CN | 1762331 A | 4/2006 |
| CN | 102000366 A | 4/2011 |
| CN | 102341133 A | 2/2012 |
| CN | 103405748 A | 11/2013 |
| CN | 103703079 A | 4/2014 |
| CN | 104474595 A | 4/2015 |
| CN | 104474595 B | 1/2017 |
| CN | 106344521 A | 1/2017 |
| EP | 0311065 B1 | 2/1994 |
| EP | 1868662 B1 | 5/2010 |
| EP | 2197419 A2 | 6/2010 |
| EP | 2209469 A2 | 7/2010 |
| EP | 2229171 A2 | 9/2010 |
| EP | 2262481 A2 | 12/2010 |
| EP | 2285363 A2 | 2/2011 |
| EP | 2288352 A2 | 3/2011 |
| EP | 2288353 A2 | 3/2011 |
| EP | 2368522 A1 | 9/2011 |
| EP | 2444074 A2 | 4/2012 |
| EP | 2444075 A2 | 4/2012 |
| EP | 2696851 A1 | 2/2014 |
| EP | 2719717 A1 | 4/2014 |
| EP | 3000463 A1 | 3/2016 |
| EP | 3085359 A1 | 10/2016 |
| EP | 2195073 B1 | 3/2017 |
| EP | 2444073 B1 | 5/2017 |
| EP | 2911647 B1 | 3/2018 |
| GB | 201505527 | 5/2015 |
| JP | 2006512312 A | 4/2006 |
| JP | 2012017329 A | 1/2012 |
| JP | 2015522649 A | 8/2015 |
| JP | 6824188 B2 | 1/2021 |
| WO | 9509613 A1 | 4/1995 |
| WO | 9858653 A1 | 12/1998 |
| WO | 9936071 A1 | 7/1999 |
| WO | 2006099409 A3 | 3/2007 |
| WO | 2008061355 A1 | 5/2008 |
| WO | 2008127411 A1 | 10/2008 |
| WO | 2008131089 A2 | 10/2008 |
| WO | 2008136856 A2 | 11/2008 |
| WO | 2009069151 A2 | 6/2009 |
| WO | 2009113972 A2 | 9/2009 |
| WO | 2009129432 A2 | 10/2009 |
| WO | 2009129433 A2 | 10/2009 |
| WO | 2009129439 A2 | 10/2009 |
| WO | 2009129453 A2 | 10/2009 |
| WO | 2009129456 A2 | 10/2009 |
| WO | 2009129460 A2 | 10/2009 |
| WO | 2009129464 A2 | 10/2009 |
| WO | 2009129491 A2 | 10/2009 |
| WO | 2009129494 A2 | 10/2009 |
| WO | 2009129509 A2 | 10/2009 |
| WO | 2009129519 A2 | 10/2009 |
| WO | 2009129527 A2 | 10/2009 |
| WO | 2009129531 A2 | 10/2009 |
| WO | 2010016832 A1 | 2/2010 |
| WO | 2010075298 A2 | 7/2010 |
| WO | 2010088697 A2 | 8/2010 |
| WO | 2011098578 A2 | 8/2011 |
| WO | 2011139594 A2 | 11/2011 |
| WO | 2012064963 A1 | 5/2012 |
| WO | 2012142318 A1 | 10/2012 |
| WO | 2013013123 A1 | 1/2013 |
| WO | 2014059558 A1 | 4/2014 |
| WO | 2014064140 A1 | 5/2014 |

(56) References Cited

FOREIGN PATENT DOCUMENTS

| WO | 2014066653 A1 | 5/2014 |
|---|---|---|
| WO | 2014137454 A1 | 9/2014 |
| WO | 2014172572 A1 | 10/2014 |
| WO | 2015015278 A1 | 2/2015 |
| WO | 2015135907 A1 | 9/2015 |
| WO | 2016123352 A1 | 8/2016 |
| WO | 2016159885 A1 | 10/2016 |
| WO | 2017019829 A1 | 2/2017 |
| WO | 2017034363 A1 | 3/2017 |
| WO | 2017075232 A1 | 5/2017 |
| WO | 2017146819 A1 | 8/2017 |
| WO | 2018009637 A1 | 1/2018 |
| WO | 2018063096 A1 | 4/2018 |
| WO | 2018067882 A1 | 4/2018 |
| WO | 2018172494 A1 | 9/2018 |
| WO | 2018227293 A1 | 12/2018 |
| WO | 2019071243 A1 | 4/2019 |
| WO | 2019136490 A1 | 7/2019 |
| WO | 2019221853 A8 | 11/2019 |
| WO | 2020046973 A1 | 3/2020 |
| WO | 2020047013 A1 | 3/2020 |
| WO | 2020210764 A1 | 10/2020 |
| WO | 2020210770 A2 | 10/2020 |
| WO | 2021178930 A1 | 9/2021 |
| WO | 2023056422 A1 | 4/2023 |

OTHER PUBLICATIONS

Tallury, et al., "Effects of solubilizing surfactants and loading of antiviral, antimicrobial, and antifungal drugs on their release rates from ethylene vinyl acetate copolymer", Dental Materials 2007 23:977-982 (Year: 2007).
Yuan, et al., "Fabrication of a Delaying Biodegradable Magnesium Alloy-Based Esophageal Stent via Coating Elastic Polymer", Materials 2016 9(384):1-11 (Year: 2016).
European Search Report dated Apr. 30, 2020; European Patent Application No. 17856916.6; 10 pages.
International Search Report and Written Opinion dated Oct. 30, 2017; International Application No. PCT/SG2017/050481; 10 pages.
International Search Report and Written Opinion dated Feb. 19, 2019; International Application No. PCT/US2018/054777; 15 pages.
International Search Report and Written Opinion dated Feb. 21, 2019; International Application No. PCT/US2018/054779; 17 pages.
International Search Report and Written Opinion dated Jul. 24, 2019; International Application No. PCT/US2019/027104; 14 pages.
International Search Report and Written Opinion dated Jul. 3, 2020; International Application No. PCT/US2020/027852; 14 pages.
International Search Report and Written Opinion dated Jun. 15, 2016, International Application No. PCT/SG/2016/050158, 17 pages.
International Search Report and Written Opinion dated Jun. 17, 2020; International Application No. PCT/US2020/027861; 11 pages.
International Search Report and Written Opinion dated May 10, 2019; International Application No. PCT/US2018/054780; 13 pages.
International Search Report and Written Opinion dated May 23, 2019; International Application No. PCT/US2019/012795; 15 pages.
International Search Report and Written Opinion dated Nov. 14, 2019; International Application No. PCT/US2019/048437; 15 pages.
International Search Report and Written Opinion dated Nov. 20, 2019; International Application No. PCT/US2019/048386; 13 pages.
Ball, et al., "Electrospun Solid Dispersions of Maraviroc for Rapid Intravaginal Preexposure Prophylaxis of HIV", Antimicrobial Agents and Chemotherapy, vol. 58, No. 8, Aug. 2014, pp. 4855-4865.
Bassi, et al., "Polymeric films as a promising carrier for bioadhesive drug delivery: Development, characterization and optimization", Saudi Pharmaceutical Journal, vol. 25, 2017, pp. 32-43.
Curley, et al., "Prolonged Regional Nerve Blockade Injectable Biodegradable Bupivacaine/Polyester Microspheres", Anesthesiology, vol. 84, 1996, pp. 1401-1410.
Drager, et al., "Prolonged Intercostal Nerve Blockade in Sheep Using Controlled-release of Bupivacaine and Dexamethasome from Polymer Microspheres", Anesthesiology, vol. 89, No. 4, Oct. 1998, pp. 969-979.

Epstein-Barash, et al., "Prolonged duration local anesthesia with minimal toxicity", PNAS, vol. 106, No. 17, Apr. 28, 2009, pp. 7125-7130.
Farid, et al., "Promote Recurrent Aphthous Ulcer Healing with Low Dose Predisolone Bilayer Mucoadhesive Buccal Film", Current Drug Delivery, vol. 14, No. 1, Jan. 9, 2017, pp. 123-125.
Fites, "Controlled Drug Release through Polymeric Films", Journal of Pharmaceutical Sciences, vol. 59, No. 5, May 1970, pp. 610-613.
Friess, Wolfgang, "Review Article: Collagen—biomaterial for drug delivery", European Journal of Pharmaceutics and Biopharmaceutics, vol. 45, 1998, pp. 113-136.
Hong, Y., et al., "Generating Elastic, Biodegradable Polyurethane/ Poly(lactide-co-glycolide) Fibrous Sheets with Controlled Antibiotic Release via Two-Stream Electrospinning", Biomacromolecules, 2008, 1200-1207.
Irfan, et al., "Orally disintegrating films: A modern expansion in drug delivery system", Saudi Pharmaceutical Journal, vol. 24, 2016, pp. 537-546.
Ito, et al., "Three-Layered Microcapsules as a Long-Term Sustained Release Injection Preparation", International Journal of Pharmaceuticals, vol. 384, No. 1-2, Jan. 1, 2010, pp. 53-59.
Jain, et al., "Injectable formulations of ply(lactic acid) and its copolymers in clinical use", Advanced Drug Delivery Reviews, vol. 107, Jul. 14, 2016, pp. 213-227.
Jethara, et al., "Sustained Release Drug Delivery Systems: a Patent Overview", Aperito Journal of Drug Designing and Pharmacology, 2014: 1:1, 15 Pages.
Jin, et al., "A PTX/nitinol stent combination with temperature-responsive phase-change 1-hexadecanol for magnetocaloric drug delivery: Magnetocaloric drug release and esophagus tissue penetration", Biomaterials, 153, 2018, pp. 49-58.
Kanagale, et al., "Formulation and Optimization of Porous Osmotic Pump-based Controlled Release System and Oxybutynin", AAPA PharmSciTech 2007, vol. 8, No. 3, Article 53, 7 Pages.
Karki, et al., "Thin films as an emerging platform for drug delivery", Asian Journal of Pharmaceutical Sciences, vol. 11, No. 5, 2016, pp. 559-574.
Kau, et al., "Sustained Release of Lidocaine from Solvent-Free Biodegradable Poly [(d,I)-Lactide-co-Glycolide] (PLGA): In Vitro and In Vivo Study", Materials, vol. 7, 2014, pp. 6660-6676.
Knecht, et al., "Mechanical testing of fixation techniques for scaffold-based tissue-engineered grafts", Journal of Biomedical Materials Research Part B: Applied Biomaterials; vol. 83, No. 1, Feb. 22, 2007, pp. 50-57.
Kolek, Matthew J., et al., "Use of an Antibacterial Envelope is Associated with Reduced Cardiac Implantable Electronic Device Infections in High-Risk Patients", Pacing and Clinical Electrophysiology, vol. 36, Mar. 2013, 354-361.
Lee, et al., "Results of a model analysis of the cost-effectiveness of liraglutide versus exenatide added to metformin, glimepiride, or both for the treatment of type 2 diabetes in the United States", Clinical Therapeutics, vol. 32, No. 10, 2010, 12 Pages.
Lei, L, et al., "5-Fluorouracil-loaded multilayered films for drug controlled releasing stent application: Drug release, microstructure, and ex vivo permeation behaviors", Journal of Controlled Release, vol. 146, No. 1, Aug. 17, 2010, pp. 45-53.
Liu, et al., "Evaluation of two polymeric blends (EVA/PLA and EVA/PEG) as coating film materials for paclitaxel-eluting stent application", J Mater Sci: Mater Med, vol. 22, 2011, pp. 327-337.
Liu, et al., "Less harmful acidic degradation of poly(lactic-co-glycolic acid) bone tissue engineering scaffolds through itania nanoparticle addition", International Journal of Nanomedicine; vol. 1, No. 4, Jan. 1, 2006, pp. 541-545.
Liu, et al., "Paclitaxel or 5-fluorouracil/esophageal stent combinations as a novel approach for the treatment of esophageal cancer", Biomaterials, vol. 53, Jun. 1, 2015, pp. 592-599.
Lee, et al., "Gemcitabine-releasing polymeric films for covered self-expandable metallic stent in treatment of gastrointestinal cancer", International Journal of Pharmaceutics, vol. 427, 2012, pp. 276-283.
McAlvin, et al., "Local Toxicity from Local Anesthetic Polymeric Microparticles", Anesth Analg., vol. 116, No. 4, Apr. 2013, pp. 794-803.

(56) References Cited

OTHER PUBLICATIONS

NIHR HSC, et al., "AIGISRx® Antibacterial Envelope for Preventing Infection in Implanted Cardiac Devices", Birmingham: NIHR Horizon Scanning Centre (NIHR HSC), Horizon Scanning Review 2012, 1 Page.

Ohri, "Inhibition by Local Bupivacaine-Releasing Microspheres of Acute Postoperative Pain from Hairy Skin Incision", URL: www.anesthesia-analgesia.org, vol. 117, No. 3, Sep. 2013, 14 Pages.

Padera, et al., "Local myotoxicity from sustained release of bupivacaine from microparticles", Anesthesiology 2008, vol. 108, No. 5, May 2008, pp. 921-928.

Pek, et al., "Sustained Release of Bupivacaine for Post-Surgical Pain Relief Using Core-Shell Microspheres", Journal of Materials Chemistry B, 2014, 9 Pages.

Rong, et al., "PLC films incorporated with paclitaxel/5-flourouracil: Effects of formulation and spacial architecture on drug release", International Journal of Pharmaceutics, vol. 427, 2012, pp. 242-251.

Roy, et al., "Effects of plasticizers and surfactants on the film forming properties of hydroxypropyl methylcellulose for the coating of diclofenac sodium tablets", Saudi Pharmaceutical Journal, vol. 17, 2009, pp. 233-241.

Santamaria, "Drug Delivery Systems for Prolonged Duration Local Anesthesia", Materials Today, vol. 20, No. 1, Jan./Feb. 2017, 22 Pages.

Seo, et al., "Polyurethane membrane with porous surface for controlled drug release in drug eluting stent", Biomaterials Research, vol. 18:15, 2014, 5 Pages.

Shaikh, "Engineering Stent Based Delivery System for Esophageal Cancer Using Docetaxel", Molecular Pharmaceutics, vol. 12, No. 7, Jul. 6, 2015, pp. 2305-2317.

Shipton, Edward A., "New Formulations of Local Anaesthetics—Part I", Anesthesiology Research and Practice, 2012, 12 Pages.

Sokolsky-Papkov, et al., "Long-Acting Poly (DL: Lactic Acid-Castor Oil) 3:7-Bupivacaine Formulation: Effect of Hydrophobic Additives", Pharmaceutical Research, Jun. 2011, 10 Pages.

Tanabe, et al., "Controlled Indomethacin Release from Mucoadhesive Film: In Vitro and Clinical Evaluations", Yakugaku Zasshi Journal of the Pharmaceutical Society of Japan, vol. 128, No. 11, Nov. 1, 2008, pp. 1673-1679.

Tarakji, et al., "Cardiac implantable electronic device infections: Presentation, management, and patient outcomes", Heart Rhythm, vol. 7, No. 8, Aug. 2010, 6 Pages.

Voigt, et al., Continued rise in rates of cardiovascular implantable electronic device infections in the United States; temporal trends and causative insights, PACE, vol. 33, Apr. 2010, 6 Pages.

Weiniger, C. F., Extended release formulations for local anaesthetic agents, Anaesthesia 2012, vol. 67, No. 8, pp. 906-916.

Yamamura, et al., Pain Relief of Oral Ulcer by Dibucaine-film, Elsevier Science Publishers, Amsterdam, NL, vol. 83, 1999, pp. 625-626.

Yan, et al., Towards nanoporous polymer thin film-based drug delivery systems, Thin Solid Films, vol. 517, 2009, pp. 1794-1798.

Zorzetto, et al., From micro- to nanostructured implantable device for local anesthetic delivery, International Journal of Nanomedicine, Jun. 8, 2016, pp. 2695-2709.

* cited by examiner

Design 4-1

Design 4-2

Design 4-3

Design 4-4

Design 4-5

Design 4-6

Design 4-7

MULTI-LAYERED POLYMER FILM FOR SUSTAINED RELEASE OF AGENTS

CROSS REFERENCE TO RELATED APPLICATIONS

The present application is a continuation of U.S. patent application Ser. No. 16/366,323, filed Mar. 27, 2019, which is a continuation of U.S. application Ser. No. 15/563,527, filed Sep. 29, 2017, now abandoned, which is a 371 of International Patent Application No. PCT/SG2016/050158, filed Mar. 31, 2016, which claims priority to foreign application GB 1505527.0, filed Mar. 31, 2015, all of which are incorporated herein by reference in their entirety.

FIELD OF INVENTION

The present invention relates to an antibiotic article that prevents infection associated with the implantation of medical devices.

BACKGROUND

Over the past decade, the usage of cardiovascular implantable electronic devices (CIEDs) has expanded dramatically, driven mostly by the increase in defibrillator therapy. Since the introduction of CIEDs, there have been numerous cases of complications, like generator migration, lead displacement and Twindler's syndrome, which are all related to the migration or displacement of the implant which leads to further intervention being necessary. A pouch to contain the CIED has been developed with the aim to create a stable environment when implanted in the body. A typical pouch used for this role is sealed at three sides and has a single opening for placing the device into said pouch.

Moreover, with the increased rate at which CIEDs are being implanted, there has been an associated increase in the number of CIED infections (Voigt et al. PACE. 2010; 33(4):414-419). Inpatient mortality associated with a CIED infection ranges from 8.4% to 11.6% (Tarakjiet Heart Rhythm. 2010; 7(8):1043-1047). The average cost to treat a CIED infection is very expensive, around US$146,000. However, since 2013 in US, the Centers for Medicare & Medicaid Services (CMS) have ceased to reimburse hospitals for the costs associated with treating infections acquired as a result of the surgical implantation of a medical device, such as a CIED, (http://www.cms.govinewsroom/mediareleasedatabase/fact-sheets/2013-fact-sheets-items/2013-08-02-3.html). Therefore, there is a significant economic impact on both the patient and the hospital in treating a hospital-acquired CIED infection. An antimicrobial article that can be attached to, or wraps around the surface of, an implantable medical device may help to reduce, prevent, or mitigate infection by eluting antimicrobial agents over time into the surrounding environment of the medical device.

A number of antimicrobial articles disclosed in International patent application publication Nos. WO 2008/127411, WO 2008/136856, WO 2009/113972, WO 2012/064963 and WO 2013/013123, have sought to address the issues associated with CIED migration and infections caused by its implantation. This Absorbable Antibacterial Envelope, developed by TYRX, Inc. (a medical device company acquired by Medtronic), is a fully absorbable sterile prosthesis designed to hold a pacemaker pulse generator or defibrillator to help create a stable environment when implanted in the body. The TYRX Absorbable Antibacterial Envelope is a mesh with large pores that is knitted from absorbable filaments (a polymer made of glycolide, caprolactone, and trimethylene carbonate) and is coated with an absorbable polyarylate polymer. The absorbable polymer coating contains two antimicrobial agents: minocycline and rifampicin.

While this system, and others like it have been proven effective for their intended use, these devices present new challenges and problems. Firstly, the envelope/pouch used in said devices has an opening that is usually bigger than the CIED to be inserted, which results in the potential risk of the CIED falling out. Moreover, these devices are designed to cater to numerous sizes of CIED, which increases the risk of smaller CIEDs falling out due to the relative rigidity and inelasticity of the material. Hence, there is a need for a new and improved design and structure that can securely hold CIEDs of various sizes.

Moreover, while the articles above go some way to dealing with infections, there are issues with the use of these antimicrobial articles. For example, the articles described above often coat both agents together on the surface, or impregnate both agents within a material, and cannot control the release of both agents together, especially when both agents have differing hydrophilicity values, as is the case with Rifampin and Minocycline. In situations where it is advisable to use more than one antimicrobial agent, it is important to control the release of both agents so that they provide the required concentration of active agent over the required period of time. Further, antimicrobial agents coated on the surface tend to be released easily, and thus there is minimal control on the rate of release of the antimicrobial agent over an extended period of time. Therefore, there is a need for an improved antibiotic article.

SUMMARY OF INVENTION

In the present invention, there is provided a soft and elastic biodegradable controlled-release antibiotic socket (e.g. a sleeve or band) which is designed to be able to securely hold different sizes of CIEDs. As such a socket (i.e. a sleeve, band or pocket) is constructed of an elastic material with at least one opening, in which the device and therefore all of the openings are smaller than the object to be inserted. The socket and its openings can be stretched to a size larger than the object to be inserted to enable ease of insertion of said device. Once said device has been inserted, the socket, which is made of an elastomeric polymeric material, is allowed to recover towards its original size, thereby holding the device inserted thereto securely. The elastic biodegradable controlled-release antibiotic socket is intended to hold a cardiac implantable electronic device (CIED) securely in order to provide a stable environment when implanted in the body; and reduce, prevent, or mitigate infection by releasing at least one antimicrobial agent during and/or after implantation in a controlled manner. The drug release is controlled by the choice of polymer, the addition of layers, tuning of the thickness of various layers, and the use of releasing agents.

Thus, in a first aspect of the invention, there is provided controlled-release antibiotic socket for securely holding an implantable medical device, comprising:
  at least one film made from at least one polymer layer, where the at least one film is formed into the socket;
  at least one antibiotic agent; and
  at least one opening in the socket, wherein
    the at least one polymer layer comprises a biodegradable elastomeric polymeric material; and
  the at least one antibiotic agent is dispersed within at least one of the at least one polymer layers and/or, when the film comprises at least two polymer layers, the at least one antibiotic agent is disposed as a separate layer between two polymer layers.

It will be appreciated that in embodiments of the socket, the socket may be in the form of a pocket with at least one opening or a sleeve/band with at least two openings. It will be further appreciated that for the socket to securely hold an implantable medical device, the socket made from the elastomeric material is smaller than the medical device to be inserted into it. This may result in the socket securely holding the medical device (e.g. a CIED device) by a resilient holding force generated from the elastomeric polymeric material that makes up the film.

In a second aspect of the invention there is provided a controlled-release antibiotic film made from at least one polymer layer for securely holding an implantable medical device, the film comprising at least one polymer layer that is made from a biodegradable elastomeric polymeric material; and at least one antibiotic agent is dispersed within at least one of the at least one polymer layers and/or, when the film comprises at least two polymer layers, the at least one antibiotic agent is disposed as a separate layer between two polymer layers.

The socket (and hence the openings) are stretchable to at least 1.1 times (e.g. from 1.2 times to 10 times) to allow for insertion of the CIED into the socket, and can recover to more than 80% to securely hold the CIED within the socket and prevent fall off. A construction of the article that may be mentioned herein comprises at least one film, which itself comprises at least one polymer layer and at least one antimicrobial agent; and at least one opening and numerous holes on the surface.

In certain embodiments of the socket and/or film of the invention:

(a) the film may have at least two polymer layers. For example, the film may have from two to ten polymer layers (e.g. from two to nine polymer layers, such as from three to seven polymer layers);

(b) the film applies a resilient force onto an object inserted into the socket;

(c) the socket or film can resiliently engage (or resiliently hold) a device after stretching or can stretch from its original size to an expanded size and return to its original size or to a size no greater than the expanded size minus (80% of the difference between expanded size and original size), optionally wherein the socket or film can stretch from its original size to an expanded size and return to its original size or to a size no greater than the expanded size minus (90% of the difference between expanded size and original size);

(d) the bioresorbable polymer of the at least one polymer layer may be selected from one or more of the group consisting of poly(DL-lactide-co-caprolactone) (DL-PLCL), or more particularly, polycaprolactone (PCL), polyglycolide (PGA), poly(L-lactic acid) (PLA), poly (trimethylene carbonate) (PTMC), polydioxanone (PDO), poly(4-hydroxy butyrate) (PHB), polyhydroxyalkanoates (PHA), poly(phosphazene), poly(phosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(glycolide-co-carolactone) (PGCL), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone cobutylacrylate, a copolymer of polyhydroxybutyrate, a copolymer of maleic anhydride, a copolymer of poly (trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives and copolymers thereof (e.g. the bioresorbable polymer of the at least one polymer layer may be selected from one or more of the group consisting of poly(DL-lactide-co-caprolactone) (DL-PLCL), or more particularly, polycaprolactone (PCL), polyglycolide (PGA), poly(L-lactic acid) (PLA), polydioxanone (PDO), poly(4-hydroxy butyrate) (PHB), polyhydroxyalkanoates (PHA), PEG and its derivatives, and their copolymers (such as selected from one or more of the group consisting of poly(DL-lactide-co-caprolactone) (DL-PLCL), or more particularly, poly(lactide-co-caprolactone) (PLCL), poly(glycolide-co-caprolactone) (PGCL) copolymer, or more preferably, polycaprolactone (PCL), polyglycolide (PGA), poly(L-lactic acid) (PLA), PEG and its derivatives and their copolymers. Particlar polymers that may be mentioned include polycaprolactone (PCL), poly (DL-lactide-co-caprolactone) (DL-PLCL), poly(glycolide-co-caprolactone) (PGCL), poly(lactide-co-caprolactone) (PLCL) and its derivatives and their copolymers));

(e) the bioresorbable polymer of the at least one polymer layer may be selected from one or more of the group consisting of poly(ester-urethane)s, poly(diol citrates), and poly(4-hydroxybutyrate)s, poly(glycerol sebacate), and star-poly(ε-caprolactone-co-D,L-lactide), poly(lactide-co-caprolactone) (PLCL), poly(DL-lactide-co-caprolactone) (DL-PLCL), poly(glycolide-co-caprolactone) (PGCL) and other biodegradable elastomer prepared through synthesis of di-, tri-, or multi-polymers, architecturally arranged in block, star, or linear structures, and prepared as thermoplastics or thermosets, their co-polymers, and mixtures or blends (e.g. PLCL, DL-PLCL and PGCL, its copolymers, and mixtures or blends, such as PLCL, its copolymers, and mixtures or blends);

(f) at least one of the at least one polymer layers may further comprise a releasing agent that is composed of one or more biocompatible hydrophilic small molecules with a hydrophobic-lipophilic balance of greater than 6 (e.g. the releasing agent is selected from one or more of the group consisting of sorbitol, xylitol, glycerin, mannitol, polyethylene glycol (PEG) having a number average molecular weight of from 200 to 2000, polysorbate and urea (e.g. selected from one or more of polysorbate 40, or more particularly, polysorbate 20, polysorbate 60 and polysorbate 80));

(g) the bioresorbable elastomeric polymeric material of one of the at least one polymer layers may be poly (lactide-co-caprolactone) (PLCL) (e.g. having a PLA to PCL ratio of from 90:10 to 60:40) or its derivatives and copolymers thereof, and/or the bioresorbable elastomeric polymeric material of one of the at least one polymer layers is poly(DL-lactide-co-caprolactone) (DL-PLCL) (e.g. having a DL-PLA to PCL ratio of from 90:10 to 50:50) or its derivatives and copolymers thereof, and/or the bioresorbable elastomeric polymeric material of one of the at least one polymer layers is poly(glycolide-co-caprolactone) (PGCL) (e.g. having a PGA to PCL ratio of from 90:10 to 10:90) or its derivatives and copolymers thereof, or, more particularly, the bioresorbable elastomeric polymeric material of one of the at least one polymer layers may be a blend of PCL and PLA (e.g. a ratio blend of PCL and PLA having a wt:wt ratio of 1:9 to 9:1);

(h) the bioresorbable elastomeric polymeric material of one of the at least one polymer layers may be a blend of DL-PLCL or PGCL or, more particularly, PLCL with a releasing agent selected from one or more of the group selected from polysorbate 20, polysorbate 60, polysorbate 80, or polyethyleneglycol having a molecular weight of 200 to 2000 Daltons in a wt:wt ratio of PLCL to releasing agent of from 25:1 to 1:9;

(i) the bioresorbable polymer of one of the at least one polymer layers may be PCL or PLA;

(j) the bioresorbable polymer of one of the at least one polymer layers may be a copolymer of poly(D,L-lactide/glycolide), such as PLGA (e.g. having a PLA to PGA ratio of from 1:9 to 9:1);

(k) the number average molecular weight of the polymer may be greater than or equal to 5,000 Daltons (e.g. from 5,000 to 500,000 Daltons or between 5,000 Daltons and 500,000 Daltons);

(l) the at least one antibiotic agent may be miscible with the bioresorbable polymer of each polymer layer in which it is present;

(m) in at least one layer of the polymer film, the at least one antibiotic agent may be homogeneously distributed within at least one of the polymer layers in which it is present (e.g. when the at least one antibiotic agent is distributed within a polymer layer, it is homogeneously distributed within said polymer layer);

(n) when the film has at least two polymer layers, the at least one antibiotic agent is distributed within at least two of the polymer layers;

(o) when the film has at least two polymer layers, the at least one antibiotic agent forms a separate layer sandwiched between the two polymer layers;

(p) when the film has at least two polymer layers and the at least one antibiotic agent is present as at least three antibiotic layers, the antibiotic layers are sandwiched between the polymer layers and a first antibiotic agent layer is sandwiched between two layers of a second antibiotic agent or between a layer of a second antibiotic agent and layer of a third antibiotic agent;

(q) when the film has at least two polymer layers and the at least one antibiotic agent is present as at least two antibiotic layers, the antibiotic layers are sandwiched between the polymer layers and a first antibiotic agent layer is sandwiched between a polymer layer and a second antibiotic layer;

(r) in at least one layer of the polymer film, the at least one antibiotic agent may be present in an amount of 0.1 wt to 99 wt %, such as from 0.1 wt % to 95 wt % of said polymer layer (e.g. from 0.1 wt % to 90 wt % or from 0.1 wt % to 80 wt %, such as from 0.1 wt % to 60 wt %), for example, in at least one layer of the polymer film, the at least one antibiotic agent may be present in an amount of from 0.1 wt % to 30 wt % (e.g. from 1 wt % to 25 wt %) of said polymer layer, optionally wherein said polymer layer is solvent cast and/or in the at least one layer of the polymer film, the at least one antibiotic agent may be present in an amount of from 10 wt % to 95 wt % (e.g. from 10 wt % to 60 wt %, or from 30 wt % to 95 wt %, such as from 40 wt % to 80 wt %) of said polymer layer, optionally wherein said polymer layer was spray coated onto a substrate;

(s) the film may further comprise holes, for example the diameter of each of the holes may be from 0.1 mm to 5 mm (e.g. from 0.3 mm to 2 mm or, more particularly, from 0.3 mm to 1 mm) or from 0.5 mm to 15 mm (e.g. from 1 mm to 20 mm), optionally:
  (i) the shape of the holes may not be uniform or the holes may be circular; and/or
  (ii) the size of the holes may not be uniform; and/or
  (iii) the holes on the socket constructed from the film may be evenly distributed throughout the film, or focused in the middle of the film (to avoid seals), or nearer to the seals;

(t) the total thickness of the film may be from 1 μm to 2000 μm (e.g. from 10 μm to 500 μm, such as from 40 μm to 300 μm).

(u) the thickness of each layer of the polymer film may be from 0.01 μm to 1000 μm (e.g. from 0.01 μm to 200 μm);

(v) the at least one antibiotic agent may be an antiseptic, a disinfectant, or, more particularly, an antimicrobial agent or an antifungal agent (e.g. the antimicrobial agent may be selected from one or more of the group consisting of tetracycline and its derivatives (such as minocycline, tigecycline and doxycycline), rifampin, triclosan, chlorhexidine, penicillins, aminoglycides, quinolones, vancomycin, gentamycine, a cephalosporin (e.g. cephalosporin), carbapenems, imipenem, ertapenem, an antimicrobial peptide, cecropin-mellitin, magainin, dermaseptin, cathelicidin, α-defensins, α-protegrins and pharmaceutically acceptable salts thereof (e.g. a combination of rifampin and another antimicrobial agent, such as a combination of rifampin and a tetracycline derivative), the antimicrobial agent may be a combination of rifampin and one or more of the group selected from minocycline, doxycycline, and tigecycline (e.g. rifampin and doxycycline, rifampin and tigecycline or, more particularly, rifampin and minocycline, such as a combination of rifampin and/or minocycline, for example, a combination of rifampin and minocycline, the ratio of rifampin to minocycline is from 1:10 to 10:1 (wt/wt) (e.g. from 2:5 to 5:2 (wt/wt)), the antifungal agent may be selected from one or more of the group consisting of azoles (such as ketoconazole, clotrimazole, miconazole, econazole, itraconazole, fluconazole, bifoconazole, terconazole, butaconazole, tioconazole, oxiconazole, sulconazole, saperconazole, clotrimazole, voriconazole, clotrimazole), allylamines (such as terbinafine), morpholines (such as amorolfine and naftifine), griseofulvin, haloprogin, butenafine, tolnaftate, nystatin, cyclohexamide, ciclopirox, flucytosine, terbinafin, amphotericin B and pharmaceutically acceptable salts thereof.

(w) the at least one antibiotic agent may be released from the antibiotic film over a period of from 1 to 30 days following implantation, for example
  (i) the at least one antibiotic agent may be released from the antibiotic film over a period of from 3 to 14 days following implantation;
  (ii) more than 10 wt % of the at least one antibiotic agent may be released within 24 h of implantation, and the remainder of the at least one antibiotic agent is released from the antibiotic film over a period of from 3 to 14 days following implantation.

(x) the film may have a single polymer layer and contains at least one antibiotic (e.g. the at least one antibiotic is minocycline and/or rifampicin);
(y) the film may have three polymer layers, with the middle layer containing at least one antibiotic (e.g. the at least one antibiotic is minocycline and/or rifampicin);
(z) the film may have three polymer layers, with the middle layer containing at least one antibiotic (e.g. the at least one antibiotic is minocycline or rifampicin) and the outer layers containing a further antibiotic (e.g. the further antibiotic is minocycline or rifampicin, provided that when the at least one antibiotic of the middle layer is minocycline, the further antibiotic of the outer layers is rifampicin and vice versa).
(aa) the film may have five polymer layers, with the middle layer containing at least one antibiotic (e.g. the at least one antibiotic is minocycline or rifampicin) and the layers immediately on top and bottom of the middle layer containing a further antibiotic (e.g. the further antibiotic is minocycline or rifampicin, provided that when the at least one antibiotic of the middle layer is minocycline, the further antibiotic of the outer layers is rifampicin and vice versa);
(bb) the film may have five polymer layers, where the layers immediately on top and bottom of the middle layer contain an antibiotic (e.g. the antibiotic is minocycline and/or rifampicin;
(cc) the film may have four polymer layers, with the middle two layers containing at least one antibiotic (e.g. the at least one antibiotic is minocycline and/or rifampicin);
(dd) the film may have two polymer layers, with the two layers each containing at least one antibiotic (e.g. the at least one antibiotic is minocycline and/or rifampicin);
(ee) the amount of the at least one antibiotic compared to the total weight of the film may be from 0.001 wt % to 30 wt %, or more particularly 0.001 wt % to 20 wt %, such as 0.001 wt % to 20 wt % (e.g. from 0.01 wt % to 5 wt %, or from 0.5 wt % to 5 wt %);
(ff) the film has two outer layers and the outer layers may have a rough and non-smooth surface.

In embodiments of the film and/or socket that may be mentioned herein:
(i) the film is a single polymer layer that contains at least one antibiotic (e.g. the at least one antibiotic is minocycline and/or rifampicin) dispersed therein; or
(ii) the film is a single polymer layer that comprises a polymeric material and a releasing agent that contains at least one antibiotic (e.g. the at least one antibiotic is minocycline and/or rifampicin) dispersed therein; or
(iii) the film has three polymer layers, such that there is a top, middle and bottom layer, where the middle layer consists only of polymeric material, and the top and bottom layers each contain at least one antibiotic (e.g. the at least one antibiotic is minocycline and/or rifampicin) dispersed therein; or
(iv) the film has three polymer layers, such that there is a top, middle and bottom layer, where the middle layer consists only of polymeric material, and the top and bottom polymer layers each comprise a polymeric material and a releasing agent that further contains at least one antibiotic (e.g. the at least one antibiotic is minocycline and/or rifampicin) dispersed therein; or
(v) the film has five layers, such that there is a top, top-intermediate, middle, bottom-intermediate and bottom layer, where the middle layer consists only of polymeric material, the top-intermediate and bottom-intermediate layers contain at least one antibiotic (e.g. the at least one antibiotic is minocycline and/or rifampicin) dispersed therein, and the top and bottom polymer layers contain at least one further antibiotic (e.g. the at least one further antibiotic is minocycline and/or rifampicin) dispersed therein, optionally wherein, when the top-intermediate and bottom-intermediate layers contain rifampicin and the top and bottom layers contain minocycline dispersed therein or vice versa; or
(vi) the film has five layers, comprising a central polymer layer, and two outer polymers layers that contain at least one antibiotic dispersed therein (e.g. the at least one antibiotic is minocycline and/or rifampicin), with an antibiotic layer (e.g. the antibiotic layers comprise minocycline and/or rifampicin) sandwiched between the central layer and each of the outer polymer layers; or
(vii) the film has five layers, such that there is a top, top-intermediate, middle, bottom-intermediate and bottom layer, where the middle layer consists only of polymeric material, the top-intermediate and bottom-intermediate polymer layers each comprise a polymeric material and a releasing agent that further contains at least one antibiotic (e.g. the at least one antibiotic is minocycline and/or rifampicin) dispersed therein, and the top and bottom polymer layers each comprise a polymeric material and a releasing agent that contains at least one further antibiotic (e.g. the at least one further antibiotic is minocycline and/or rifampicin) dispersed therein, optionally wherein, when the top-intermediate and bottom-intermediate polymer layers contain rifampicin and the top and bottom polymer layers contain minocycline dispersed therein or vice versa; or
(viii) the film has seven layers, such that there is a top, top-intermediate, top-middle-intermediate, middle, bottom-middle-intermediate, bottom-intermediate and bottom polymer layer, where the middle layer consists only of polymeric material, the top-middle-intermediate and bottom-middle-intermediate polymer layers each comprise a polymeric material that contains at least one antibiotic (e.g. the at least one antibiotic is minocycline and/or rifampicin) dispersed therein, the top-intermediate and bottom-intermediate polymer layers each comprise a polymeric material and a releasing agent, and the top and bottom polymer layers each further contain at least one further antibiotic (e.g. the at least one antibiotic is minocycline and/or rifampicin) dispersed therein, optionally wherein, when the top-middle-intermediate and bottom-middle-intermediate polymer layers contain rifampicin, the top and bottom polymer layers contain minocycline dispersed therein or vice versa; or
(ix) the film has seven layers, such that there is a top, top-intermediate, top-middle-intermediate, middle, bottom-middle-intermediate, bottom-intermediate and bottom polymer layer, where the middle layer consists only of polymeric material, the top-middle-intermediate and bottom-middle-intermediate layers consist of at least one antibiotic (e.g. the at least one antibiotic is minocycline and/or rifampicin), the top-intermediate and bottom-intermediate layers comprise a polymeric material and a releasing agent, and the top and bottom layers each comprise a polymeric material and at least one further antibiotic (e.g. the at least one antibiotic is minocycline and/or rifampicin) dispersed therein, optionally wherein, when the top-middle-intermediate and bottom-middle-intermediate polymer layers contain rifampicin, the top and bottom polymer layers contain minocycline dispersed therein or vice versa; or (x) the film has seven layers, such that there is a top, top-intermediate, top-middle-intermediate, middle, bottom-middle-intermediate, bottom-intermediate and bottom polymer layer, where the middle layer consists only of polymeric material, the top-middle-intermediate and bottom-middle-intermediate polymer layers each comprise a polymeric material that contains at least one antibiotic (e.g. the at least one antibiotic is minocycline and/or rifampicin) dispersed therein, the top-intermediate and bottom-intermediate polymer layers each comprise a polymeric material and a releasing agent, and the top and bottom polymer layers each comprise a polymeric material and a releasing agent and each further contain at least one further antibiotic (e.g. the at least one further antibiotic is minocycline and/or rifampicin) dispersed therein, optionally wherein, when the top-middle-intermediate and bottom-middle-intermediate polymer layers contain rifampicin, the top and bottom polymer layers contain minocycline dispersed therein or vice versa; or (xi) the film has seven layers, such that there is a top, top-intermediate, top-middle-intermediate, middle, bottom-middle-intermediate, bottom-intermediate and bottom polymer layer, where the middle, top-intermediate and bottom-intermediate polymer layers consists only of polymeric material, the top-middle-intermediate and bottom-middle-intermediate polymer layers each comprise a polymeric material that contains at least one antibiotic (e.g. the at least one antibiotic is minocycline and/or rifampicin) dispersed therein, and the top and bottom polymer layers each contain at least one further antibiotic (e.g. the at least one further antibiotic is minocycline and/or rifampicin) dispersed therein, optionally wherein, when the top-middle-intermediate and bottom-middle-intermediate polymer layers contain rifampicin, the top and bottom polymer layers contain minocycline dispersed therein or vice versa; or (xii) the film has seven layers, with the middle layer being a biodegradable elastic polymer layer, the layers immediately on top and bottom of the middle layer containing at least one antibiotic (e.g. the at least one antibiotic is minocycline and/or rifampicin), the layers on top of the antibiotic layers are polymer layers, and the outer layers are each comprise a polymeric material and a further antibiotic (e.g. the further antibiotic is minocycline or rifampicin, provided that when the at least one antibiotic of the intermediate layer is minocycline, the further antibiotic of the outer layers is rifampicin and vice versa); or (xiii) the film has seven layers, such that there is a top, top-intermediate, top-middle-intermediate, middle, bottom-middle-intermediate, bottom-intermediate and bottom polymer layer, where the middle, top-intermediate and bottom-intermediate polymer layers consists only of polymeric material, the top-middle-intermediate and bottom-middle-intermediate polymer layers each comprise a polymeric material that contains at least one antibiotic (e.g. the at least one antibiotic is minocycline and/or rifampicin) dispersed therein, and the top and bottom polymer layers each comprise a polymeric material and a releasing agent and each contain at least one further antibiotic (e.g. the at least one further antibiotic is minocycline and/or rifampicin) dispersed therein, optionally wherein, when the top-middle-intermediate and bottom-middle-intermediate polymer layers contain rifampicin, the top and bottom polymer layers contain minocycline dispersed therein or vice versa; or (xiv) the film has three polymer layers, where the middle polymer layer contains at least one antibiotic (e.g. the at least one antibiotic is minocycline and/or rifampicin) dispersed therein; or (xv) the film has three polymer layers, where the middle polymer layer contains at least one antibiotic (e.g. the at least one antibiotic is minocycline and/or rifampicin) dispersed therein, and the top and bottom layers contain at least one further antibiotic (e.g. the at least one further antibiotic is minocycline or rifampicin; optionally wherein, when the at least one antibiotic of the middle layer is minocycline, the at least one further antibiotic of the outer layers is rifampicin and vice versa) dispersed therein; or (xvi) the film has three polymer layers, where the middle polymer layer comprises a polymeric material and a releasing agent that contains at least one antibiotic (e.g. the at least one antibiotic is minocycline and/or rifampicin) dispersed therein, and the top and bottom layers each comprise a polymeric material and a releasing agent that contains at least one further antibiotic dispersed therein (e.g. the at least one further antibiotic is minocycline or rifampicin; optionally wherein, when the at least one antibiotic of the middle layer is minocycline, the at least one further antibiotic of the outer layers is rifampicin and vice versa); or (xvii) the film has five polymer layers, such that there is a top, top-intermediate, middle, bottom-intermediate and bottom layer, where the middle layer contains at least one antibiotic (e.g. the at least one antibiotic is minocycline or rifampicin) dispersed therein, and the top-intermediate and bottom-intermediate polymer layers contain at least one further antibiotic dispersed therein (e.g. the at least one further antibiotic is minocycline or rifampicin, optionally wherein that when the at least one antibiotic of the middle layer is minocycline, the at least one further antibiotic of the top-intermediate and bottom-intermediate layers is rifampicin and vice versa); or (xviii) the film has five polymer layers, such that there is a top, top-intermediate, middle, bottom-intermediate and bottom layer, where the middle layer contains at least one antibiotic (e.g. the at least one antibiotic is minocycline or rifampicin) dispersed therein, and the top-intermediate and bottom-intermediate polymer layers contain at least one further antibiotic dispersed therein (e.g. the at least one further antibiotic is minocycline or rifampicin, provided that when the at least one antibiotic of the middle layer is minocycline, the at least one further antibiotic of the top-intermediate and bottom-intermediate layers is rifampicin and vice versa), and the top and bottom layers each comprise a polymeric material and a releasing agent; or (xix) the film has five polymer layers, such that there is a top, top-intermediate, middle, bottom-intermediate and bottom layer, where the top-intermediate and bottom-intermediate polymer layers contain at least one antibiotic ((e.g. the further antibiotic is minocycline and/or rifampicin); or (xx) the film has four polymer layers, where the middle two polymer layers containing at least one antibiotic (e.g. the at least one antibiotic is minocycline and/or rifampicin); or (xxi) the film has four polymer layers, where the middle two polymer layers containing at least one antibiotic (e.g. the at least one antibiotic is minocycline and/or rifampicin) dispersed therein, and the two outermost layers comprise a polymeric material and a releasing agent; or (xxii) the film has two polymer layers, where the two polymer layers each contain at least one antibiotic (e.g. the at least one antibiotic is minocycline and/or rifampicin); or (xxiii) the film has two polymer layers, where one of the polymers layers further comprises at least one antibiotic (e.g. the at least one antibiotic is minocycline and/or rifampicin) and the other polymer layer further comprises at least one antibiotic (e.g. the at least one antibiotic is minocycline and/or rifampicin) and a releasing agent, optionally the antibiotic in the layer also containing the releasing agent is minocycline and the other layer contains rifampicin or vice versa; or (xxiv) the film has five layers, such that there is a top, top-intermediate, middle, bottom-intermediate and bottom layer, where the middle layer consists only of polymeric material, the top-intermediate and bottom-intermediate polymer layers each comprise a polymeric material and at least one antibiotic (e.g. the at least one antibiotic is minocycline and/or rifampicin) dispersed therein, and the top and bottom polymer layers each comprise a polymeric material, a releasing agent and at least one further antibiotic (e.g. the at least one further antibiotic is minocycline and/or rifampicin) dispersed therein, optionally wherein, when the top-intermediate and bottom-intermediate polymer layers contain rifampicin the top and bottom polymer layers contain minocycline dispersed therein or vice versa; or (xxv) the film has four layers, such that there is a top, top-middle, bottom-middle and bottom layer, where the top layer comprises a polymeric material, a releasing agent and at least one antibiotic (e.g. the at least one further antibiotic is minocycline and/or rifampicin), the top-middle layer consists of at least one antibiotic (e.g. the at least one further antibiotic is minocycline and/or rifampicin), the bottom-middle layer comprises a polymeric material and at least one antibiotic (e.g. the at least one further antibiotic is minocycline and/or rifampicin), and the bottom layer consists only of polymeric material.

It will be appreciated that when the term "at least one antibiotic" is used above in relation to a film or socket made therefrom having more than one layer, it may refer to the use of the same (or same mixture of) antibiotic in all layers that contain an antibiotic, and/or to different antibiotics (and/or to different mixtures of antibiotics) in layers of the film or socket made therefrom.

In embodiments of the socket described herein, the implantable medical device may be a cardiovascular implantable electronic device (CIED).

In further aspects of the invention, there is provided:

(i) a socket or film as set out in the first and second aspects of the invention (and their various embodiments, whether alone or in any suitable combination) for use in treating or preventing infection and associated diseases and disorders;

(ii) a socket or film as set out in the first and second aspects of the invention (and their various embodiments, whether alone or in any suitable combination), in the manufacture of a medicament for use in the treatment or prevention of infection and associated diseases and disorders; or (iii) a method of treatment comprising the step of placing at least part of an implantable medical device into a socket as set out in the first aspect of the invention (and its various embodiments, whether alone or in any suitable combination) to provide a coated implantable medical device and placing the coated implanted medical device into a subject to treat or prevent infection and associated diseases and disorders arising from said implantation.

In embodiments of the above aspects, the film may be used to cover at least part of the surface of a medical device that is then implanted into a subject.

In a further aspect of the invention, there is provided an implantable medical device comprising a medical device and socket as set out in the first aspect of the invention (and its various embodiments, whether alone or in any suitable combination), wherein the film covers a part or the whole of the medical device and is suitable for reducing or preventing migration of the medical device within the body following implantation. For example, the film may be provided in the shape of an envelope or pouch to surround part or whole of the medical device. In certain embodiments, the device may further comprise an additional active agent (e.g. a growth factor, an anti-inflammatory, or anaesthetic agent) coated onto whole or part of an exposed surface of the film.

In yet a further aspect of the invention, there is provided a process for making a socket or film as set out in the first and second aspects of the invention (and their various embodiments, whether alone or in any suitable combination), wherein when the socket is made from a film having two or more polymer layers or the film has two or more polymer layers, the film is prepared by the use of one or more of heat-melting, heat-compression, spray coating, dip coating, chemical grafting, electrostatic adsorption, chemical crosslinking to join the polymer layers together.

DESCRIPTION

Figure 1:
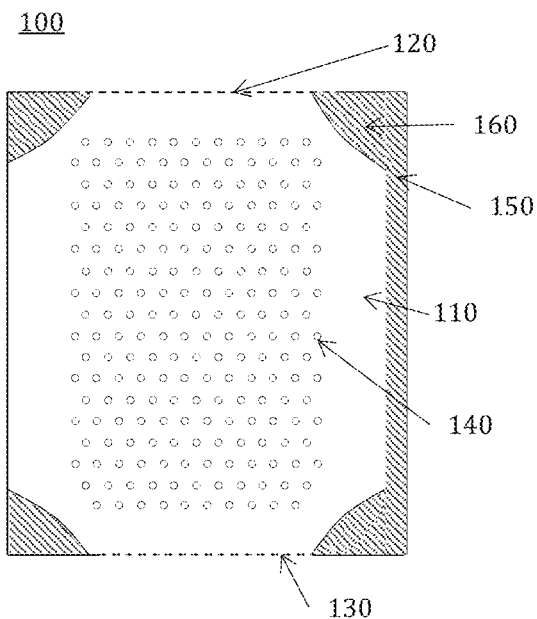
FIGS. 1 to 3 depict schematic illustrations of an article designed according to an embodiment of the invention (a socket to surround a medical device) with holes.

The antibiotic socket of the current invention relates to a socket made from an elastic film material (comprising one or more elastomeric polymer layers), with at least one opening in the socket. The socket is smaller than the objects it is intended to hold and so it is stretched to a size to permit the object to be inserted and then recovers towards its original size (due to the elastic material that is made from), such that it securely holds the object inserted thereto (e.g. resiliently engages, holds or secures the object). The secure/resilient securing of the object inserted significantly reduces the possibility of the CIED falling out. In addition, the socket (or the film the socket is made from) may also have a rough surface, which aids in securing the object to the socket and may also help the socket secure the object following implantation into the body. In addition, the rough surface may also prevent the film/socket made therefrom from becoming adhered to a surface (i.e. sticking to a surface), for example the roughness may ensure that the inner surfaces of the socket do not stick to each other and thereby enables easy opening of the socket to insert a device. Further, the socket (or the film the socket is made from) may also contain numerous holes that may help to increase friction and reduce migration of the implant as well as allow outflow of exudates. The design of the socket is thus able to securely hold various sizes of medical devices (e.g. CIEDs) and prevent or reduce migration of the device during implantation, without risk of the device falling out of the socket.

In addition, the antibiotic socket of the current invention may comprise a single layer or multiple layers of a biodegradable/bioresorbable polymer film with at least one antibiotic agent contained within at least one of the polymer layers, or the antibiotic may be disposed as a separate layer encapsulated by at least two polymer layers to form a control-release matrix to provide a required eluting profile for the at least one antibiotic agent for a desired time period. The single layer or multilayer structure also can be incorporated with other functional agents, such as anti-inflammatory, or anaesthetic agents or a growth factor agent.

Thus there is provided a controlled-release antibiotic socket for securely holding an implantable medical device, comprising:

at least one film made from at least one polymer layer, where the at least one film is formed into the socket;
at least one antibiotic agent; and
at least one opening in the socket, wherein
the at least one polymer layer comprises a biodegradable elastomeric polymeric material; and
the at least one antibiotic agent is dispersed within at least one of the at least one polymer layers and/or, when the film comprises at least two polymer layers, the at least one antibiotic agent is disposed as a separate layer between two polymer layers.

When used herein, the term "socket" is intended to mean a device that is intended to securely hold a separate object by surrounding the whole or part of said separate object (e.g. the socket may leave parts of the object uncovered to enable further connectivity of the object). It will be appreciated from the context of the invention, that the socket is intended to be smaller than the object it is intended to hold and accomplishes the secure holding by its elastic nature, such that it may be stretched to a size larger than the object to be held and then recovers towards its original size once the object to be held has been placed within the socket. As will be apparent, the socket requires at least one opening to permit an object to be inserted within it and so the socket may also be described as a pocket when it has a single opening. In alternative arrangements, the socket may have two openings and so may also be called a sleeve or band. It will be appreciated that the socket may contain more than two openings too.

The socket is made from at least one film. Thus, there is also provided a film made from at least one polymer layer for securely holding an implantable medical device, the film comprising:

at least one polymer layer that is made from a biodegradable elastomeric polymeric material; and
at least one antibiotic agent is dispersed within at least one of the at least one polymer layers and/or, when the film comprises at least two polymer layers, the at least one antibiotic agent is disposed as a separate layer between two polymer layers.

As is apparent, both the socket and film are elastic, in that they can be stretched/deformed in any direction and recover towards their original size and shape. This property enables the socket to securely hold an object placed therein. This may be accomplished by the resilient force applied to the object inserted into the socket by the elastomeric polymeric material that comprises the film. Thus, the socket or film can resiliently engage or resiliently hold a device inserted into a socket formed from the film after stretching. In addition or alternatively, the socket or film can stretch from its original size to an expanded size and return to its original size or to a size no greater than the expanded size minus (80% of the difference between expanded size and original size), optionally wherein the socket or film can stretch from its original size to an expanded size and return to its original size or to a size no greater than the expanded size minus (90% of the difference between expanded size and original size).

The controlled release antibiotic socket of the current invention provides enhanced stability of the object (i.e. the CIED) within the socket, reducing the possibility of the object falling out of the socket, and is able to effectively achieve that for a wide range of objects (i.e. CIEDs of different sizes) with one size of socket. The selection of an elastic polymeric material is an intricate balance of elastic modulus and strain recovery. Certain polymers with high elasticity (low elastic modulus) have poor strain recovery, and would not be able to hold an object well. Other polymers that have relatively low elasticity (high elastic modulus) are not suitable for the construction of a sleeve that can securely hold different sizes of object. The design of the sleeve aids in enhancing the stability of the object (i.e. CIED) within. Thus care need to be exercised in selecting the materials used to form the polymer film.

The controlled-release elastic biodegradable antibiotic film that makes up the socket in the first embodiment of the invention may comprise a single layer or multiple layers with at least one antibiotic agent contained within at least one of the layers to form a controlled-release matrix to provide a required eluting profile for the at least one antibiotic agent for a desired time period. One or more of the layers may contain a releasing agent to enhance control of release of at least one antibiotic agent within the same layer or at other layers of the film. The single layer or multilayer structure also can be incorporated with other functional agents, such as anti-inflammatory, or anaesthetic agents or a growth factor agent.

Thus, there is provided a controlled-release antibiotic film made from at least one polymer layer for securely holding an implantable medical device, the film comprising at least one polymer layer that is made from a biodegradable elastomeric polymeric material; and at least one antibiotic agent is dispersed within at least one of the at least one polymer layers and/or, when the film comprises at least two polymer layers, the at least one antibiotic agent is disposed as a separate layer between two polymer layers.

The controlled release antibiotic socket and films of the current invention provide enhanced control of drug eluting characteristics compared with previous drug eluting articles. This is achieved tuning of various factors, for example using additional layers (polymer layers or a layer of drug), where the active agent(s) are incorporated into different layer(s) (whether dispersed within a polymer layer, or forming a separate layer sandwiched between polymer layers), controlling the polymers used, controlling the thickness of the layers, the drug-polymer composite ratio, addition of releasing agent(s), and a layered structure designed to control the release rate of the active agent(s). It will be appreciated that these features allow for the design of a polymer film where the release profile of two or more active agents, having different release profiles from a polymer film, can be independently controlled. This allows for the active agents to be released at the same time, or to have one or other of the active agents release more quickly in comparison to other active agents etc.

When used herein, the terms "antibiotic film" and "antibiotic agent" may refer to an antimicrobial, an antifungal, an antiseptic or a disinfecting film and/or agent. In particular examples, "antibiotic film" and "antibiotic agent" may refer to an antimicrobial or antifungal agent.

Examples of antimicrobial agents that may be mentioned herein include tetracycline and its derivatives (such as minocycline, tigecycline and doxycycline), rifampin, triclosan, chlorhexidine, penicillins, aminoglycides, quinolones, vancomycin, gentamycine, a cephalosporins (e.g. cephalosporin), carbapenems, imipenem, ertapenem, an antimicrobial peptide, cecropin-mellitin, magainin, dermaseptin, cathelicidin, α-defensins, α-protegrins, pharmaceutically acceptable salts thereof and combinations thereof. Particular combinations of antimicrobial agents that may be mentioned include a combination of rifampin and another antimicrobial agent, such as a combination of rifampin and a tetracycline derivative (e.g. minocycline, doxycycline, and tigecycline, such combinations including rifampin and doxycycline, rifampin and tigecycline or, more particularly, rifampin and minocycline).

For example, when the antimicrobial agent is a combination of rifampin and minocycline, the ratio of rifampin to minocycline is from 1:10 to 10:1 (wt/wt) (e.g. from 2:5 to 5:2(wt/wt)).

When used herein "rifampicin" and "rifampin" are used interchangeably herein to refer to the active agent having CAS number 13292-46-1, or salts and/or solvates thereof.

Examples of antifungal agents that may be mentioned herein include azoles (such as ketoconazole, clotrimazole, miconazole, econazole, itraconazole, fluconazole, bifoconazole, terconazole, butaconazole, tioconazole, oxiconazole, sulconazole, saperconazole, clotrimazole, voriconazole, clotrimazole), allylamines(such as terbinafine), morpholines (such as amorolfine and naftifine), griseofulvin, haloprogin, butenafine, tolnaftate, nystatin, cyclohexamide, ciclopirox, flucytosine, terbinafin, amphotericin B and pharmaceutically acceptable salts thereof.

When used herein, the term "releasing agent" or "hydrophilic small molecules" may refer to natural or synthetic chemical compounds with a molecular weight of less than 2000 Daltons, which are able to dissolve or dislodge from a matrix when in contact with water or in physiological conditions. Examples of releasing agents that may be mentioned herein include sorbitol, xylitol, glycerin, mannitol, polyethylene glycol (PEG) having a number average molecular weight of from 200 to 2000 Daltons, polysorbate and urea or any molecule (e.g. one that has a molecular weight of less than 2000 Daltons) with a hydrophobic-lipophilic balance of greater than 6.

When used herein, the term "polymer layer" may refer to a formulated composition which forms a solid or semi-solid film, with/without an antibiotic agent (as defined herein), with a controlled thickness. The combination of polymer layers may serve as a drug reservoir exhibiting drug control-release behaviour. In certain embodiments of the invention that may be mentioned herein, when an antibiotic agent is present in the polymeric layer, the polymeric material may comprise at least 1 wt % (e.g. at least 2 wt %, such as at least 5 wt %) of the polymer layer.

When used herein "antibiotic layer" may refer to a defined layer of an antibiotic layer laid on the surface of a polymer layer and comprising at least one or more antibiotic materials, but which is substantially free of a polymeric material (i.e. there may be less than 0.5 wt % of a polymeric material as a minor impurity in said layer), or more particularly, there is an absence of polymeric material in the antibiotic layer. For the avoidance of doubt, the antibiotic layer cannot be on a surface of a polymer layer that is directly in contact with the environment in a completed film, that is, each antibiotic layer is ultimately encapsulated between two polymer layers. This encapsulation may be direct (e.g. an antibiotic layer is sandwiched between two polymer layers) or indirect (e.g. where two antibiotic layers are laid on top of each other and encapsulated between two polymer layers, such that each antibiotic layer is in direct contact with one of the polymer layers). It will be appreciated that the antibiotic layers may be continuous or discontinuous, such that the antibiotic layer can be encapsulated within the polymer layers (e.g. the footprint of the antibiotic layer is adjusted so that it is smaller than the footprint of the polymer layers that encapsulate it). In addition, it will be appreciated that the antibiotic layer may take the form of a particulate layer on the surface of a polymeric substrate layer.

While it is possible for the film of the current invention to provide beneficial effects as a single layer of film, particular embodiments of the invention relate to a film has at least two polymer layers. For example, the film may have from two to nine layers, such as from three to seven layers (e.g. from three to five layers), whether polymer layers only or a combination of polymer layers and antibiotic layers, provided that the antibiotic layers are not the outer layers of the film. In embodiments that may be mentioned herein, the film may have from two to nine polymer layers, such as from three to seven polymer layers (e.g. from three to five polymer layers).

When used herein, the terms "bioresorbable polymer" and "biodegradable polymer" refers to a material that can be at least partially broken down or, more particularly, fully degraded by contact with a bodily fluid, with the breakdown products being either eliminated from the body as waste or used by the body in further metabolic processes (e.g. anabolic processes).

Examples of bioresorbable polymers include poly(DL-lactide-co-caprolactone) (DL-PLCL), or more particularly, poly(lactide-co-caprolactone) (PLCL), polycaprolactone (PCL), polyglycolide (PGA), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), poly(phosphate ester), poly(amino acid), polydepsipeptides, poly(butylene succinate) (PBS), polyethylene oxide, polypropylene fumarate, polyiminocarbonates, poly(D,L-lactic acid), polyglycolic acid, poly(L-lactide-co-D,L-lactide), poly(L-lactide-co-glycolide) (PLGL), poly(D,L-lactide-co-glycolide), poly(gycolide-trimethylene carbonate), poly(glycolide-co-caprolactone) (PGCL), poly(ethyl glutamate-co-glutamic acid), poly (tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol, hydroxypropylmethylcellulose and cellulose derivatives, polysaccharides, such as hyaluronic acid, chitosan, starch, proteins such as gelatin, collagen or PEG derivatives and combinations thereof.

Particular bioresorbable polymers that may be mentioned include poly(DL-lactide-co-caprolactone) (DL-PLCL), or more particularly, polycaprolactone (PCL), polyglycolide (PGA), poly(L-lactic acid) (PLA), polydioxanone (PDO), poly(4-hydroxy butyrate) (PHB), polyhydroxyalkanoates (PHA), PEG and its derivatives, and their copolymers (e.g. selected from one or more of the group consisting of poly(DL-lactide-co-caprolactone) (DL-PLCL), polycaprolactone (PCL), polyglycolide (PGA), poly(L-lactic acid) (PLA), PEG and its derivatives and their copolymers). Further polymers that may be mentioned herein include, poly(ester-urethane)s, poly(diol citrates), poly(4-hydroxybutyrate)s, poly(glycerol sebacate), and star-poly(ε-caprolactone-co-D,L-lactide), poly(lactide-co-caprolactone) (PLCL), poly(glycolide-co-caprolactone) (PGCL) and other biodegradable elastomer prepared through synthesis of di-, tri-, or multi-polymers, architecturally arranged in block, star, or linear structures, and prepared as thermoplastics or thermosets, their co-polymers, and mixtures or blends. Particular polymers that may be mentioned herein include DL-PLCL, PGCL and PLCL, their copolymers, and mixtures or blends thereof.

When used herein, the term "elastic polymer" refers to a material that can resist a distorting influence or stress and can return to towards its original size and shape when the stress is removed. For example, the elastic polymer may be stretched up to 10 times its original size in any direction (e.g. from 1.1 times to 4 times its original size) and may then recover at least to 80%, such as at least 90% of its original size following release of the stretch. For example, when stretching a film to size B (a difference of size C) from size A results in the film returning to a maximum size of B−(0.8×C) following stretching and release, where C is B−A, such as a maximum size of B−(0.9×C). That is, if one stretches a film from 0.1 cm to 0.11 cm (difference of 0.01 cm), the resulting film will have maximum size of 0.11−(0.8×0.01)=0.102 cm if the film recovers at least to 80% of its original size or will have a maximum size of 0.101 cm if the film recovers to at least 90% of its original size following stretching. It will be appreciated that the film may recover to its original size or almost to its original size.

The antibiotic film can be prepared as a single polymer, a polymer blend or copolymer, with one or more layers. In particular embodiments of the film or socket made therefrom:

(a) the bioresorbable elastomeric polymeric material of one of the at least one polymer layers may be a blend of PCL and PLA (e.g. a ratio blend of PCL and PLA having a wt:wt ratio of 1:9 to 9:1), or a blend of PCL and PGA (e.g. a ratio blend of PCL and PGA having a wt:wt ratio of 1:9 to 9:1); or (b) the bioresorbable elastomeric polymeric material of one of the at least one polymer layers may be PCL, or a copolymer of poly(DL-lactide/caprolactone), such as DL-PLCL (e.g. having a DL-PLA to PCL ratio of from 1:9 to 9:1), or a copolymer of poly(lactide/caprolactone) such as PLCL (e.g. having a PLA to PCL ratio of from 1:9 to 9:1), or a copolymer of poly(glycolide/caprolactone) such as PGCL (e.g. having a PCL to PGA ratio of from 1:9 to 9:1); or (c) the bioresorbable elastomeric polymeric material of one of the at least one polymer layers may be poly(DL-lactide-co-caprolactone) (DL-PLCL), or more particularly a blend of PCL and PLA (e.g. a ratio blend of PCL and PLA having a wt:wt ratio of 1:9 to 9:1), poly(ester-urethane)s, poly(diol citrates), and poly(4-hydroxybutyrate)s, poly(glycerol sebacate), star-poly(ε-caprolactone-co-D,L-lactide), poly(lactide-co-caprolactone) (PLCL), poly(glycolide-co-caprolactone) (PGCL) or other biodegradable elastomer; or (d) the bioresorbable elastomeric polymeric material of one of the at least one polymer layers may be one or more copolymers (such as selected from one or more of the group consisting of polycaprolactone (PCL), polyglycolide (PGA), poly(L-lactic acid) (PLA), PEG and its derivatives and their copolymers)), such as a copolymer of poly (glycolide/caprolactone) or poly(lactide/caprolactone) (e.g. having a PLA to PCL ratio of from 9:1 to 6:4) or its derivatives and copolymers thereof; or (e) the bioresorbable elastomeric polymeric material of one of the at least one polymer layers may be a blend of PLCL and PCL (e.g. a ratio blend of PLCL and PCL having a wt:wt ratio of 1:9 to 9:1).

Further polymeric elastomeric materials that may be mentioned herein include:

a) the bioresorbable elastomeric polymeric material of one of the at least one polymer layers is poly(lactide-co-caprolactone) (PLCL) (e.g. having a PLA to PCL ratio of from 90:10 to 60:40) or its derivatives and copolymers thereof; and/or b) the bioresorbable elastomeric polymeric material of one of the at least one polymer layers is poly(DL-lactide-co-caprolactone) (DL-PLCL) (e.g. having a DL-PLA to PCL ratio of from 90:10 to 50:50) or its derivatives and copolymers thereof; and/or c) the bioresorbable elastomeric polymeric material of one of the at least one polymer layers is poly(glycolide-co-caprolactone) (PGCL) (e.g. having a PGA to PCL ratio of from 90:10 to 10:90) or its derivatives and copolymers thereof; and/or d) the bioresorbable elastomeric polymeric material of one of the at least one polymer layers is a blend of PLCL or DL-PLCL or PGCL with a releasing agent selected from one or more of the group selected from polysorbate 20, polysorbate 40, polysorbate 60, polysorbate 80, or polyethyleneglycol having a molecular weight of 200 to 2000 Daltons in a wt:wt ratio of PLCL or DL-PLCL or PGCL to releasing agent of from 25:1 to 1:9.

Particular polymers that may be mentioned herein include PLCL, DL-PLCL and PGCL.

It will be appreciated, that the polymer layers described above may be combined to form a single multilayer film. This film may only have polymer layers, or may also have antibiotic layers interspersed between the polymer layers, provided that the antibiotic layers are ultimately encapsulated between two polymer layers.

In particular embodiments of the invention as disclosed herein, the number average molecular weight of the polymer may be greater than or equal to 5,000 Daltons, such as greater than 5000 Daltons (e.g. from 5,000 to 500,000 Daltons).

The antibiotic film include may include a releasing agent in at least one layer of the film or the film that comprises a component part of the socket. The releasing agent may be present in at least one of the at least one layers of the film, whether the layer is a polymer layer or an antibiotic layer, or may be present in more than one of the layers that make up the film, up to the total number of layers in the film. It will be appreciated, that when present, the releasing agent may be a single releasing agent or may be more than one releasing agent. When there is more than one releasing agent (e.g. 2 to 10 releasing agents), the releasing agents may be mixed together to form a blend that may be applied to one or more of the layers of the film as described above. Alternatively, when there are at least two releasing agents (e.g. 3 to 9 releasing agents), each releasing agent may be applied to separate layers of the film, provided that more than two layers of the film are intended to contain a releasing agent. Yet further alternatively, when there are at least three releasing agents (e.g. 4 to 10 releasing agents), at least two blends (e.g. 3 to 9 blends) of releasing agents may be prepared and each blend may be applied to separate layers of the film, provided that more than two layers of the film are intended to contain a releasing agent. When present in a layer, the releasing agent may be present in an amount from 0.1 wt % to 50 wt % of said layer.

The antibiotic film includes at least one antibiotic agent which is distributed in at least one layer of polymer. The antibiotic agent may be distributed within one or more polymer layers of the antibiotic film (e.g. heterogeneously or, more particularly homogeneously distributed). Therefore, while not necessary, in particular embodiments of the current invention the at least one antibiotic agent is miscible with the bioresorbable polymer of each polymer layer in which it is present. For example:
(i) when the film has at least two polymer layers, the at least one antibiotic agent is distributed within at least two of the polymer layers; and/or
(ii) when the film has at least two polymer layers, the at least one antibiotic agent forms a separate layer sandwiched between the two polymer layers; and/or
(ii) when the film has at least two polymer layers and the at least one antibiotic agent is present as at least three antibiotic layers, the antibiotic layers are sandwiched between the polymer layers and a first antibiotic agent layer is sandwiched between two layers of a second antibiotic agent or between a layer of a second antibiotic agent and layer of a third antibiotic agent; and/or
(iii) when the film has at least two polymer layers and the at least one antibiotic agent is present as at least two antibiotic layers, the antibiotic layers are sandwiched between the polymer layers and a first antibiotic agent layer is sandwiched between a polymer layer and a second antibiotic layer.

In at least one layer of the polymer film, the at least one antibiotic agent may be present in an amount of from 0.1 wt % to 99 wt %, such as from 0.1 wt % to 95 wt % of said polymer layer (e.g. from 0.1 wt % to 90 wt % or from 0.1 wt % to 80 wt %, such as from 0.1 wt % to 60 wt %), for example, in at least one layer of the polymer film, the at least one antibiotic agent may be present in an amount of from 0.1 wt % to 30 wt % of said polymer layer, optionally wherein said polymer layer is solvent cast and/or in the at least one layer of the polymer film, the at least one antibiotic agent may be present in an amount of from 10 wt % to 95 wt % (e.g. from 10 wt % to 60 wt %, or from 30 wt % to 95 wt %, such as from 40 wt % to 80 wt %) of said polymer layer, optionally wherein said polymer layer was spray coated onto a substrate.

The antibiotic film can be formed as a single layer film or a multilayer film composite. The composite consists of at least one type of biodegradable polymer and at least one antibiotic agent. Each polymer layer can be formed from one biodegradable polymer or polymer blends. For example, the outer layer of biodegradable polymer film incorporated with or without an agent to encourage tissue growth on the surface, such as collagen, a middle layer of biodegradable polymer incorporated with an antibiotic agent, and a third layer of biodegradable polymer, with no active agent. Another multilayer film composite can be a layer of biodegradable polymer with or without a growth factor agent, three layers of a biodegradable polymer composite comprising an antibiotic agent, and followed by a layer of biodegradable polymer film with or without a growth factor agent. The antibiotic agents in the three layers can be the same or different in content and concentration distribution.

Further examples of the antibiotic film include:
(a) a film having a single polymer layer and contains at least one antibiotic (e.g. the at least one antibiotic is minocycline and/or rifampicin);
(b) a film having three polymer layers, with the middle layer containing at least one antibiotic (e.g. the at least one antibiotic is minocycline and/or rifampicin);
(c) a film having three polymer layers, with the middle layer containing at least one antibiotic (e.g. the at least one antibiotic is minocycline or rifampicin) and the outer layers containing a further antibiotic (e.g. the further antibiotic is minocycline or rifampicin, provided that when the at least one antibiotic of the middle layer is minocycline, the further antibiotic of the outer layers is rifampicin and vice versa);
(d) a film having five polymer layers, with the middle layer containing at least one antibiotic (e.g. the at least one antibiotic is minocycline or rifampicin) and the layers immediately on top and bottom of the middle layer containing a further antibiotic (e.g. the further antibiotic is minocycline or rifampicin, provided that when the at least one antibiotic of the middle layer is minocycline, the further antibiotic of the outer layers is rifampicin and vice versa);
(e) a film having five polymer layers, where the layers immediately on top and bottom of the middle layer contain an antibiotic (e.g. the further antibiotic is minocycline and/or rifampicin;
(f) a film having four polymer layers, with the middle two layers containing at least one antibiotic (e.g. the at least one antibiotic is minocycline and/or rifampicin);
(g) a film having two polymer layers, with the two layers each containing at least one antibiotic (e.g. the at least one antibiotic is minocycline and/or rifampicin).

Yet further examples are provided as embodiments (i) to (xxv) in the summary of invention section hereinabove and are omitted in full here for brevity. It will be noted from these examples that while the layering design may be symmetrical, it does not need to be. That is, the layering design may be asymmetrical in nature and an example of this is provided as example (xxv) in the summary of invention section hereinabove.

In at least one layer of the antibiotic polymer film and sockets made therefreom, the at least one antibiotic agent is present in an amount of from 0.1 wt % to 99 wt %, such as from 0.1 wt % to 95 wt % of said polymer layer (e.g. from 0.1 wt % to 90 wt % or from 0.1 wt % to 80 wt %, from 0.1 wt % to 60 wt %, such as from 0.1 wt % to 30 wt % or from 10 wt % to 60 wt %). The actual amount present within each polymer layer may vary depending on the way that the layer of film was prepared. For example, when the polymer layer is solvent cast the at least one antibiotic agent may be present in an amount of from 0.1 wt % to 30 wt % of said polymer layer, and when the polymer layer was formed by spray coating it onto a substrate, the at least one antibiotic agent may be present in an amount of from 10 wt % to 95 wt % (e.g. from 10 wt % to 60 wt %, or from 30 wt % to 95 wt %, such as from 40 wt % to 80 wt %).

As noted hereinbefore, the film and sockets made therefrom, may contain one or more layers of the one or more antibiotic agent that are ultimately encapsulated between two polymer layers. In such separate antibiotic layers, the at least one antibiotic agent may be present in an amount of from 10 wt % to 100 wt % of said layer. Said layer may further comprise releasing agent or other pharmaceutically acceptable adjuvants, diluents or disperants.

The at least one antibiotic agent may make up from 0.001 wt % to 30 wt %, or more particularly 0.001 wt % to 20 wt %, such as 0.001 wt % to 20 wt % (e.g. from 0.01 wt % to 5 wt %, or from 0.5 wt % to 5 wt %) of the weight of the entire film (i.e. all layers of the film).

It will be appreciated that for the film/socket to prove effective, it has to release the one or more antibiotic agents over an extended period of time in a controlled manner. For example, the at least one antibiotic agent is released from the antibiotic film over a period of from 1 to days following implantation or, more particularly, over a period of from 3 to 14 days following implantation.

Particular films and sockets made therefrom that may be mentioned herein include an antibiotic film/socket where more than 10 wt % of the at least one antibiotic agent is released within 24 hours of implantation, with the entirety of the at least one antibiotic agent being released from the antibiotic film over a period of from 3 to 14 days following implantation.

It will be appreciated that the antibiotic films and the sockets made therefrom of the current invention can be used in medicine. For example, the antibiotic films mentioned herein can be used in treating or preventing infection and associated diseases and disorders. In addition, the films mentioned herein may be used in:

(a) the manufacture of a medicament for use in the treatment or prevention of infection and associated diseases and disorders; and
(b) a method of treatment comprising the step of applying the controlled-release antibiotic film to a subject to treat or prevent infection and associated diseases and disorders.

The antibiotic films and sockets made therefrom mentioned herein may be used to cover at least part of the surface of a medical device that is then implanted into a subject, as described in more detail below.

As mentioned hereinbefore, the films and the sockets made therefrom may be applied to an implantable medical device, where the resulting device comprises a medical device and an antibiotic film in the form of a socket as described herein, wherein the socket covers a part or the whole of the medical device and is suitable for reducing or preventing migration of the medical device within the body following implantation. For example, the sockets made from the film may be provided in the shape of an envelope, pouch, pocket, sleeve or band to surround part or whole of the medical device. The device may further comprise an additional active agent (e.g. a growth factor) coated onto whole or part of an exposed surface of the film. An embodiment of the device is described below in relation to FIG. 1.

The term "implantable medical device", when used herein refers to a medical device that can be implanted transdermally, or to any indwelling medical device that includes a transdermal component. Examples of an implantable medical device that may be mentioned herein include arteriovenous shunts, left ventricular assist devices, cardiovascular implantable electronic devices (CIEDs), tissue expanders, gastric lap bands, spinal cord stimulators, intrathecal infusion pumps, deep brain stimulators, gastric electrical stimulators, sacral nerve stimulators, and vagus nerve stimulators, amongst others.

FIG. 1 is a schematic illustration of an antibiotic film shaped into an article substrate that can be coupled to an implantable medical device for implantation into a site of subject's body. The article may be used to secure an implantable device at the desired site within the subject's body, by helping to anchor the device into the surrounding tissue or part of the tissue. The article is also able to inhibit bacterial growth due to the presence of the antibiotic agent within the film.

Figure 2:
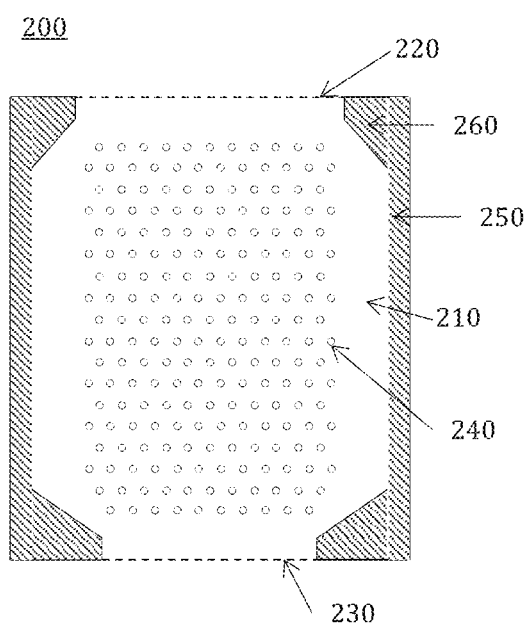
Figure 3:
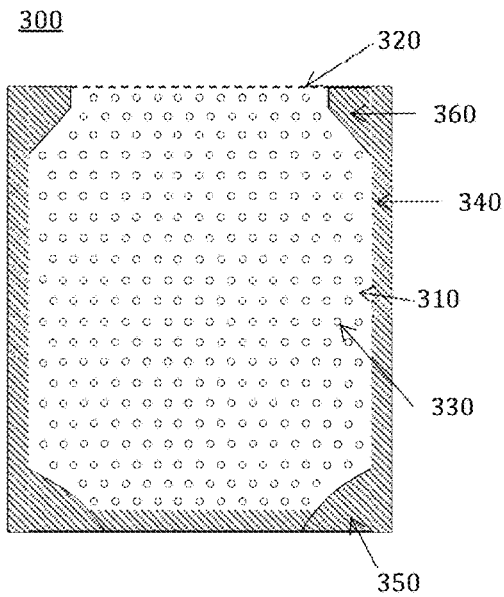
Figure 4A:
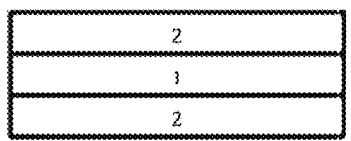
FIGS. 4A to 4G depict examples of layered designs according to embodiments of the current invention.
Figure 4B:
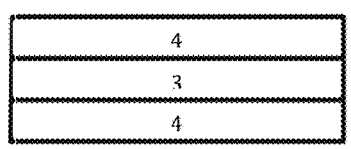
Figure 4C:
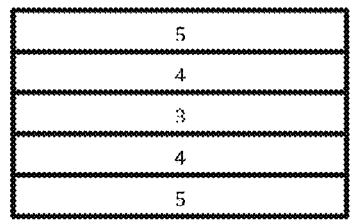
Figure 4D:
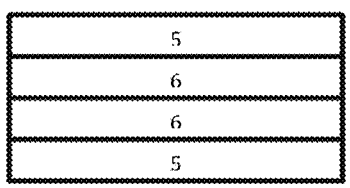
Figure 4E:
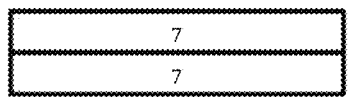
Figure 4F:
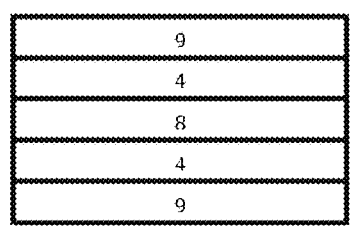
Figure 4G:
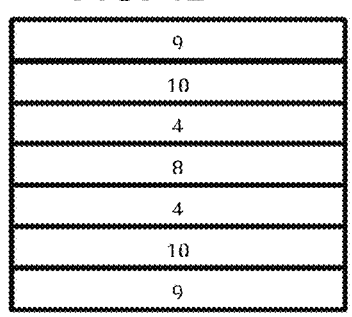

In FIG. 1, the socket 100 according to the current invention, comprising a controlled-release antimicrobial film 110 as hereinbefore defined, has two openings 120 and 130 that may be fully or partially open, and so may be described as a band or sleeve, as well as a socket. The socket itself and hence the openings 120/130 are smaller than the object to be inserted into and held by the socket. The socket may also, as illustrated, contain a plurality of holes 140 in the film 110. As depicted, the socket is made from a single film and so only requires a single side-seal 150 and may also comprise curved seal corners 160. It will be appreciated that the socket may be manufactured using more than one film, which may then result in additional side-seals being required. As shown in FIG. 1, the openings 120/130 may be of the same size. However, it is specifically contemplated that the openings may also be of different sizes. In certain embodiments, the holes may be from 0.1 mm to 5 mm (e.g. from 0.3 mm to 2 mm or from 0.3 mm to 1 mm). As shown in FIG. 1, the holes may have a uniform shape and size (e.g. all are circular in shape of the same size). However, it is specifically contemplated that the holes may be irregular in shape (each hole being of an undefined shape) or be of any shape (e.g. random defined shapes) and that the size of the holes may not be uniform. The holes may be focused in the middle (avoiding seals and openings) as shown in FIGS. 2 and 3, or evenly distributed throughout the band or nearer to the seals and openings as shown in FIG. 1. According to certain embodiments of the invention, the sleeve may be formed by sealing at one end, as shown in FIG. 1, or sealed at multiple ends. The corner seals may be curved, as shown in FIG. 1, angled or squared.

In FIG. 2, the socket 200 according to the current invention is made from a controlled-release antimicrobial film 210 (i.e. any film as defined hereinbefore), with two openings 220 and 230, a plurality of holes (e.g. one or more holes) 240, two-side seals 250 and angled sealed corners 260. It will be appreciated that the socket is smaller than the object to be inserted therein (i.e. a CIED) and may be capable of housing a range of different sizes of CIED. As shown in FIG. 2, the openings may be of different sizes; however it is specifically contemplated that the openings may also be of the same size. In certain embodiments, the holes may be from 0.1 mm to 5 mm (e.g. from 0.3 mm to 2 mm). The socket of FIG. 2 may be formed by sealing two films together at two ends, as shown in FIG. 2 to form a sleeve or band-like structure. According to further embodiments of the invention, the corner seals may be angled, as shown in FIG. 2, or curved or squared. It is also contemplated that the corner seals may be angled in any technically suitable manner.

In FIG. 3, there is provided a socket in the form of a pocket 300 according to the current invention, comprising a controlled-release antimicrobial film 310 (i.e. any film described hereinbefore), with one opening 320, a plurality of holes (e.g. one or more holes) 330, a three-side seal 340, curved sealed corners 350 and angled sealed corners 360. As shown in FIG. 3, the pocket may be formed by sealing at least two films together at three ends, leaving a single end open to act as an opening. It will be appreciated that all of the ends may be sealed together and a new opening created by cutting an opening of suitable dimensions into the sealed film (this may apply using a single film as well as more than two films).

When used herein, the term "article" may refer to the overall medical device unit, that is the film and implantable medical device, or it may refer to the film shaped as a socket (i.e. a mesh, pouch, bag, envelope, sleeve, band, pocket or receptacle (all of which may be with or without holes)), that can fully or partially cover an implantable medical device.

As noted above, the socket (e.g. 300 of FIG. 3) may be in the form of an envelope with an opening 320 to allow insertion of an implantable device into the film and to permit insertion of accessories, such as leads or wires. The surface of the article 300 may also contain holes 330 within the film 310, with all possible shapes and dimensions to reduce mass of pouch and to enhance the release of the active agent into the surrounding tissue efficiently. It will be appreciated that this is generically applicable to other forms of sockets described or contemplated herein. The size, shape and weight of the article can vary according to the implantation requirement. Alternatively, the film may be cut into strips an applied piece-meal so as to cover whole or part of the medical device. In such examples, the film may be applied by any method of bonding, such as by the use of an adhesive, heat bonding or adhesion caused by the nature of the film itself (e.g. in the manner of attaching a plastic paraffin film to an object).

The sockets of FIGS. 1-3, are configured to (1) reduce device migration or erosion; (2) securely hold the implanted medical device within the article to reduce the risk of it falling out; (3) securely hold various sizes of medical device to reduce the risk of it falling out; (4) eliminate direct contact between the implanted medical device and the tissue layer; and (5) release antibiotic agent within a desired period at the required eluting rate. This is achieved by the properties of the socket and the antibiotic film(s) that form the socket of the current invention.

The antibiotic article is a versatile platform, which can be capable of different functions. For example, the controlled release of the antibiotic agent is sufficient to prevent or reduce bacteria colonization on the surface of the implantable medical device. In addition, the device can also be incorporated with other functions, such as the enhancement of tissue attachment on the outer surface of the envelope by coating the surface of the film in direct contact with body tissue with one or more growth factors.

It will be appreciated that the article can be designed to have any shape and size according to the needs of the medical device to be implanted.

The film of the article described in FIG. 1 can be formed by at least one layer or several layers of biodegradable polymer film. At least one of said polymers layers contains an antibiotic agent. However, different layers may have different functions, such as a drug incorporation layer, a drug release control layer, a layer to promote tissue-ingrowth after implantation etc.

FIG. 4 provides various multilayer films according to aspects of the invention. The single layer to multiple layer films may have a total thickness of the film is from 1 μm to 2000 μm (e.g. from 10 μm to 500 μm, such as from 40 μm to 300 μm). In general, for a multilayer film (or a single layer film), the thickness of each layer of the polymer film may be from 0.01 μm to 1000 μm (e.g. from 0.01 μm to 200 μm).

The multilayer designs of various embodiments of the invention are depicted in FIGS. 4A-4G. The design shown in FIG. 4A (also referred to herein as "design 4-1" shows a 3-layer film, in which the middle layer may be a piece of drug-containing biodegradable polymer film with at least one or more drugs 1, the outer two layers 2 may be biodegradable polymer films further comprising a releasing agent blend, but without any active agent which can be formed by the same or different polymer materials. The design shown in FIG. 4B (also referred to herein as "design 4-2") depicts a 3-layer film, in which the middle layer is a piece of drug-containing biodegradable polymer film with at least one or more drugs 3, the surface of this film (3) is coated with a layer of drug-containing biodegradable polymer layers with one or more drugs 4. The design shown in FIG. 4C (also referred to herein as "design 4-3") depicts a 5-layer film, in which the middle three layers are similar to design 4-2, with the outer two surface layers being biodegradable polymer layers that may contain a releasing agent and are with/without drug 5. The design shown in FIG. 4D (also referred to herein as "design 4-4") shows a 4-layer film, in which the middle two layers 6 contain a drug, with the films in the outer surfaces 5 are biodegradable polymer layers that may contain a releasing agent and are with/without drug. The design shown in FIG. 4E (also referred to herein as "design 4-5") shows a 2-layer film, in which both layers are with one or two drugs 7. The design shown in FIG. 4F (also referred to herein as "design 4-6") shows a 5-layer film, in which the middle layer may be a piece of biodegradable elastic polymer film without any active agent or releasing agent 8, the surface of this film (8) is coated with a layer of drug-containing biodegradable polymer layers with one or more drugs 4, and the two outer surface layers are a blend of polymer and releasing agent that may or may not contain a drug 9. The design shown in FIG. 4G (also referred to herein as "design 4-7") shows a 7-layer film in which the middle layer may be a piece of biodegradable elastic polymer film without any active agent or releasing agent 8, the surface of this film (8) is coated with a layer of drug-containing biodegradable polymer layers with one or more drugs 4, the two layers immediately after is a blend of polymer with or without releasing agent 10, and the outer surface layer is a blend of polymer and releasing agent that may or may not contain a drug 9.

These films may be prepared by making each layer separately and stacking these individual film layers together through heat-melting, heat-compression, chemical grafting, electrostatic adsorption, chemical crosslinking etc. Alternatively or additionally, a film layer may also be used as a substrate and be spray- or dip-coated on one or both surfaces to form a further polymer layer (or layers). The preferred film preparation methods are film casting, spray coating and heat compression.

The various embodiments described above are not intended to be limiting and the principles provided can be used to generate, further designs having different drug or polymer compositions and/or different film properties that do not departs from the spirit and scope of the current invention (e.g. that do not depart from the scope of the currently claimed invention). Designs that may be mentioned herein include those where the film comprises at least 2-layers. The main purpose of the invention is to be able to control the drug release profile of one or more active agents independently in a drug-polymer matrix for different drugs. As different active agents have different potencies and different hydrophilicity, it is rather challenging to control the drug release profile by using one polymer formulation for each drug. The designs shown in FIG. 4 enable one to control the drug release profile of different active agents separately to achieve a desired drug release profile for both agents.

The antibiotic article can be tailored to different shapes and dimension to partially cover or fully wrap an implantable medical device. The thickness of each layer ranges from 0.01 µm to 1000 µm (e.g. from 0.01 µm to 200 µm).

The antibiotic article is bioabsorable, which can provide a temporary anchorage for implantable medical device and gradually be absorbed/excreted by the body to provide comfort to patient. The article eliminates direct contact between the implanted medical device and tissue layer and may reduce the implanted device's migration or erosion. The article is fully resorbable with good mechanical strength.

The growth of tissue on the surface of the antibiotic article can be controlled by incorporating a layer of growth factor on the surface according to surgeons' needs.

The sockets and/or films of the current invention provide the following advantages:
(1) the elastic socket can hold the device tightly to prevent medical device from dropping-off when implanted—especially when used to fit various sizes of CIED;
(2) the socket can securarly hold a medical device and prevent or reduce migration of device during implantation;
(3) drug release control can be tuned independently according to desired drug release profile for each drug within the film—a particular challenge when there is more than one antibiotic agent to be released;
(4) the antibiotic agents are distributed throughout the polymer layers to which they form an integral part, making the antibiotic agent more stable and reducing fragility problems associated with coating a layer of drug onto a polymer surface;
(5) the burst phase of the antibiotic agent(s) are easier to control using the film technology of the current invention, allowing more consistent control of the delivery of the antibiotic agents initially and in the subsequent controlled release phase.

EXAMPLES

General Preparation

To illustrate the kinetics of drug release, a sample of the film was cut into a 2 cm×2 cm size, which was immersed in a vial containing 4 mL of PBS buffer (as the elution medium) for continuous drug elution testing. The vial was placed in a 37° C. incubator shaker. At periodic intervals, the elution medium was withdrawn for reverse phase HPLC analysis to determine the eluted amount of rifampicin and minocycline and replaced with fresh PBS solution (4 mL). The cumulative drug release was calculated and plotted (see FIGS. 4-6).

Table 1 and FIG. 4 list a series of designs that were used in the examples. The table lists a number of polymers that can be used to generate compositions according to the current invention (whether alone or in combination), as well as antibiotics. It will be understood that alternative polymers and antibiotics may be used.

TABLE 1

Film matrix with rifampin (R) and minocycline (M)

| Film code | Design | Polymer | Antibiotics |
|---|---|---|---|
| 1-1 | 4-1 | PLCL, PLA, PLGA | M |
| 1-2 | 4-1 | PLCL, PLA, PLGA | R |
| 1-3 | 4-2 | PLCL, PLA, PLGA | M |
| 1-4 | 4-2 | PLCL, PLA, PLGA | R |
| 1-5 | 4-3 | PLCL, PLA, PLGA | M |
| 1-6 | 4-3 | PLCL, PLA, PLGA | R |
| 1-7 | 4-4 | PLCL, PLA, PLGA | M |
| 1-8 | 4-4 | PLCL, PLA, PLGA | R |
| 1-9 | 4-5 | PLCL, PLA, PLGA | M |
| 1-10 | 4-5 | PLCL, PLA, PLGA | R |
| 1-11 | 4-6 | PLCL, PLA, PLGA | M |
| 1-12 | 4-6 | PLCL, PLA, PLGA | R |
| 1-13 | 4-7 | PLCL, PLA, PLGA | M |
| 1-14 | 4-7 | PLCL, PLA, PLGA | R |
| 1-15 | Single Layer, with releasing agent | PLCL | M |
| 1-16 | Single Layer, with releasing agent | PLCL | R |
| 1-17 | Single Layer, without releasing agent | PLCL | M |
| 1-18 | Single Layer, without releasing agent | PLCL | R |

Example 1 (Design 4-1, Film Codes 1-1 and 1-2)

1-A Film Casting for Drug-Resorbable Film 1.8 g PLCL resin, 700 mg of sorbitol and 160 mg of minocycline (film code 1-1; rifampicin for film code 1-2) were dissolved in 10 mL acetone/ethanol solvent mixture of the ratio of 5:5 v/v. The mixture was mixed evenly for more than 4 hours. After the mixing, the solution was homogeneous and 5 mL of the solution was then poured onto a glass plate and drawn by a film applicator to form a film upon drying. The film was removed from the glass plate after the film was completely dry, following evaporation of the solvent.

1-B Film Casting for Control Layer Film

Similarly, 1.8 g PLCL resin and 50 mg sorbitol were dissolved in 10 mL of acetone. A homogeneous solution was poured onto a glass plate and drawn by a film applicator to form a film following evaporation of the solvent. The film was then removed from the glass plate.

1-C Films Compression

A composition according to design 4-1 was prepared using two films according to 1-B sandwiching a film according to 1-A. The resulting stack of films were aligned and compressed by a heat compressor at 60° C., 6 MPa for 50 seconds.

Example 2 (Design 4-2, Film Codes 1-3 and 1-4)

2-A Film Casting for Drug-Biodegradable Film 1.8 g PLCL/PLC resin (2:8 weight ratio) and 160 mg of minocycline (film code 1-3; rifampicin for film code 1-4) were dissolved in 10 mL acetone/ethanol solvent mixture having a ratio of 5:5 v/v. The film casting procedure was the same as described in Example 1-A.

2-B Spray Coating of Drug—PLGA Mixture

Similarly, 180 mg PLGA resin and 20 mg of minocycline (film code 1-3; rifampicin for film code 1-4) were dissolved in 10 mL acetone/ethanol solvent mixture having the ratio of 5:5 v/v. The mixture was spray coated onto the film prepared in 2-A, using 2 mL of the prepared solution, by repeatedly passing the spray nozzle over both sides of film 2A with the same number of passes.

Example 3 (Design 4-3, Film Code 1-5 and 1-6)

The middle three layers were prepared by following procedure in Example 2. The two outer layers were prepared by following Example 1-B. The stack of 5 layers of films were aligned properly and compressed by a heat compressor at 60° C., 6 MPa for 50 seconds.

Example 4 (Design 4-4, Film Code 1-7 and 1-8)

The outer two layers were prepared by following Example 1-B. The two middle drug-polymer layers were prepared by following Example 2-B. The resulting films were aligned properly and compressed by a heat compressor at 60° C., 6 MPa for 50 seconds.

Example 5 (Design 4-5, Film Code 1-9 and 1-10)

The two layers were prepared by following Example 1-A and 2-A. Film compression procedure is the same as 1-C.

Example 6 (Design 4-6, Film Code 1-11 and 1-12)

6-A Film Compression for Elastic Biodegradable Polymer Film

PLCL resin was heat compressed at 150° C., 60 Mpa for 1 minute.

6-B Spray Coating of Drug—PLGA Mixture 180 mg PLGA resin and 20 mg of minocycline (film code 1-11; rifampicin for film code 1-12) were dissolved in 10 mL acetone/ethanol solvent mixture having the ratio of 5:5 v/v. The mixture was spray coated onto the film prepared in 6-A, using 2 mL of the prepared solution, by repeatedly passing the spray nozzle over both sides of film 6A with the same number of passes.

6-C Film Casting for Blend of Small Molecules Drug Film 1.8 g PLCL resin, 250 mg of polysorbate and 160 mg of minocycline(film code 1-1; rifampicin for film code 1-2) were dissolved in 10 mL acetone/ethanol solvent mixture of the ratio of 5:5 v/v. The mixture was mixed evenly for more than 4 hours. After the mixing, the solution was homogeneous and 5 mL of the solution was then poured onto a glass plate and drawn by a film applicator to form a film upon drying. The film was removed from the glass plate after the film was completely dry, following evaporation of the solvent.

6-D Films Compression

A composition according to design 4-6 was prepared using two films according to 6-C sandwiching a film 6-A coated according to 6-B. The resulting stack of films were aligned and compressed by a heat compressor at 60° C., 6 MPa for 50 seconds.

Example 7 (Design 4-7, Film Code 1-13 and 1-14)

7-A Film Casting for Blend of Small Molecule Control Film 1.8 g PLCL resin and 50 mg of polysorbate were dissolved in 10 mL acetone/ethanol solvent mixture of the ratio of 5:5 v/v. The mixture was mixed evenly for more than 4 hours. After the mixing, the solution was homogeneous and 5 mL of the solution was then poured onto a glass plate and drawn by a film applicator to form a film upon drying. The film was removed from the glass plate after the film was completely dry, following evaporation of the solvent.

7-B Films Compression

A composition according to design 4-7 was prepared using two films according to 7-A sandwiching a film 6-A coated according to 6-B. The stack is further sandwiched between two films according to 6-C. The resulting stack of films were aligned and compressed by a heat compressor at 60° C., 6 MPa for 50 seconds.

Example 8 (Single Layer, with Releasing Agent, Film Code 1-15 and 1-16)

Film preparation procedure is the same as Example 1-A to prepare a single layer.

Example 9 (Single Layer without Releasing Agent, Film Code 1-17 and 1-18)

9-A Film Casting for Drug-Resorbable Film

PLCL resin and 160 mg of minocycline(film code 1-1; rifampicin for film code 1-2) were dissolved in 10 mL acetone/ethanol solvent mixture of the ratio of 5:5 v/v. The mixture was mixed evenly for more than 4 hours. After the mixing, the solution was homogeneous and 5 mL of the solution was then poured onto a glass plate and drawn by a film applicator to form a film upon drying. The film was removed from the glass plate after the film was completely dry, following evaporation of the solvent.

Example 10 (Mixed Drug)

Figure 6:
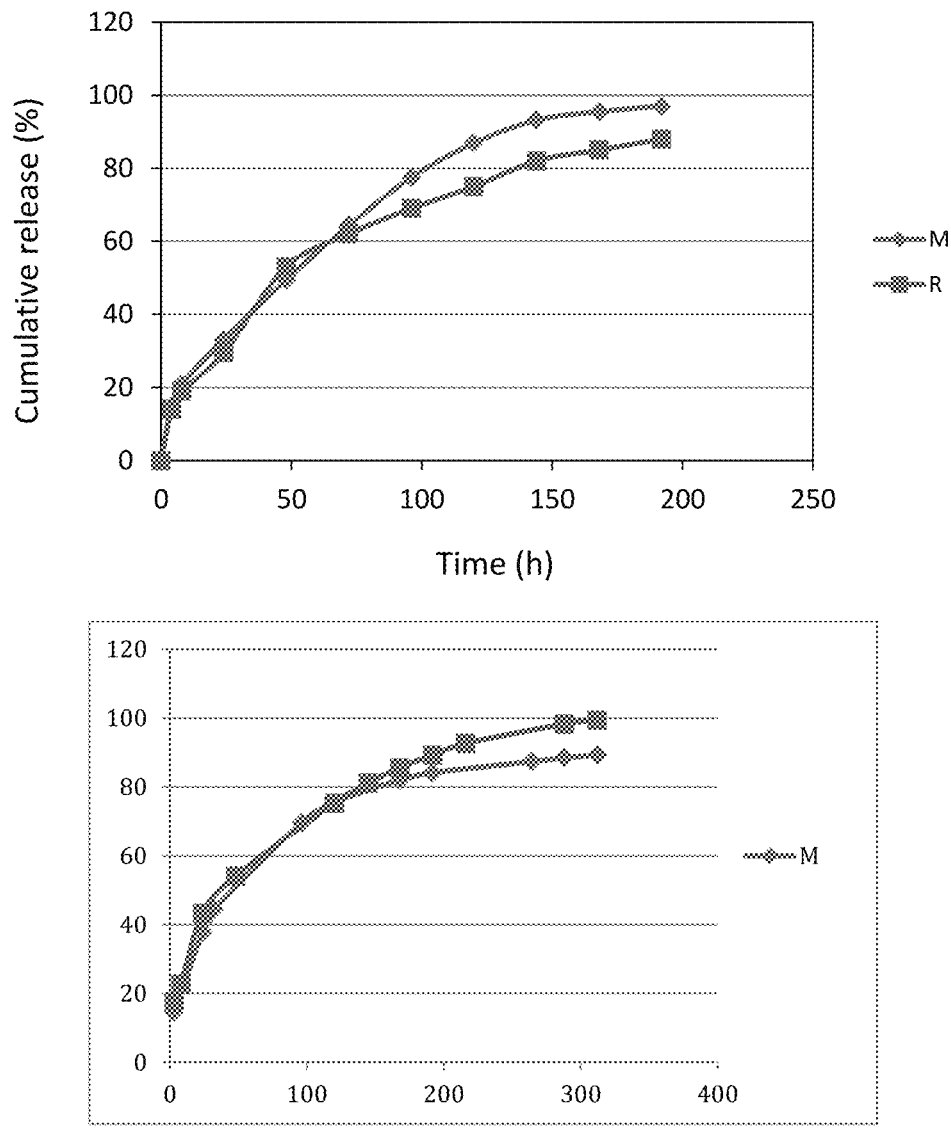
FIG. 6 depicts the cumulative release profile of minocycline and rifampin in a single film according to an embodiment of the current invention.
Figure 7:
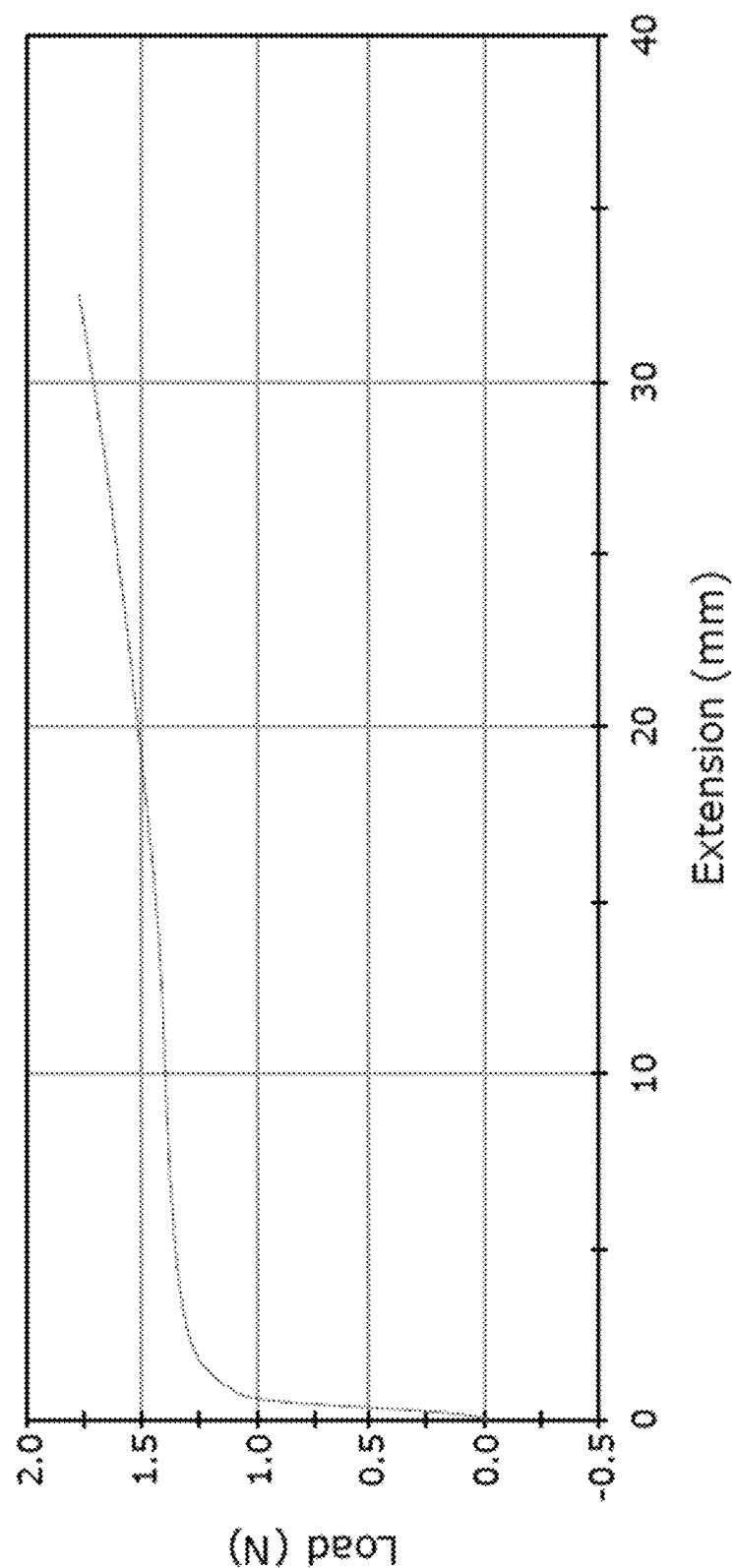
FIG. 7 depicts a tensile curve of an article.

The film was prepared by following the protocol in Example 3. The middle layer was prepared by using a drug mixture of 120 mg minocycline and 160 mg rifampin. The two intermittent layers were prepared by spray coating of minocycline by following Example 2-B. The outer two layers were prepared by following Example 1-B. The stack of 5 layers of films were aligned properly and compressed by a heat compressor at 60° C., 6 MPa for 50 seconds. The cumulative releasing profiles of two antibiotics are shown in FIG. 6.

Example 11

Figure 5A:
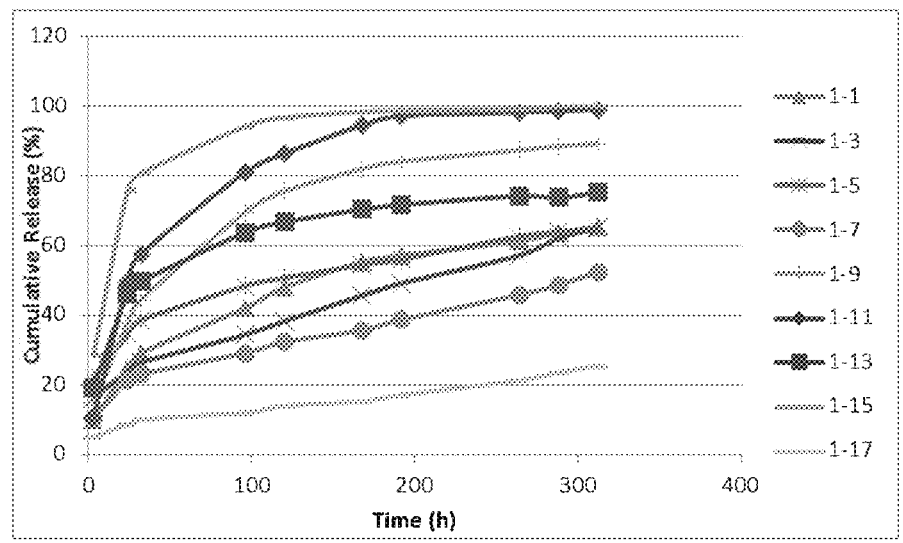
FIGS. 5A and 5B depict the cumulative release profile of minocycline (5A) and rifampin (5B) in the exemplified embodiments of the invention.
Figure 5B:
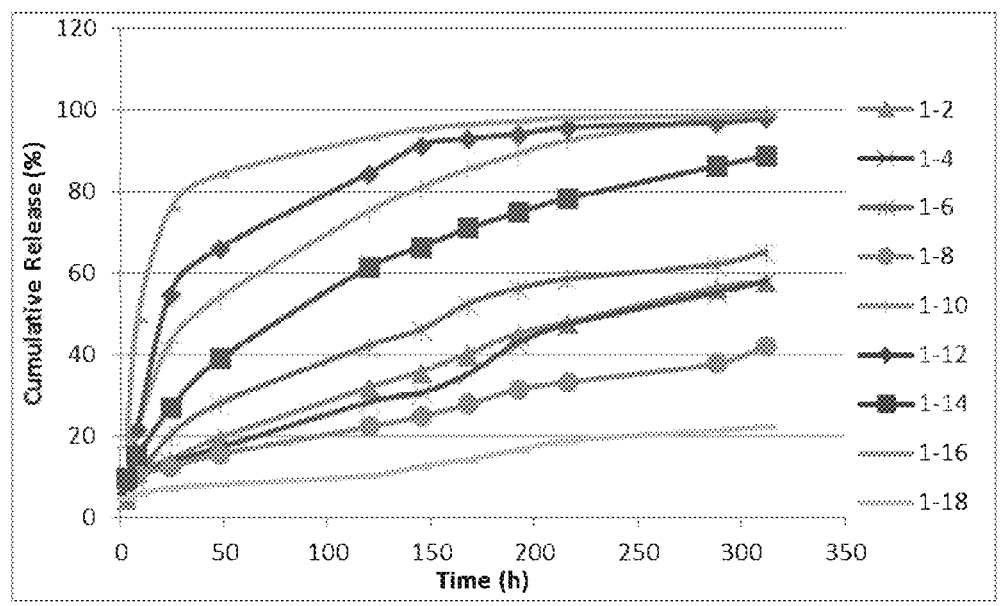

FIGS. 5A-5B show the cumulative release of two antibiotics from different layered film designs and single films prepared in Examples 1 to 9 (film codes 1-1 to 1-18). The drug density of both antibiotics is between 0.05 mg to 0.1 mg/cm$^2$. As shown in FIGS. 5A-B, for single drug film, the absence of releasing agent results in a film with very slow release, while the presence of releasing agent gives a high initial burst with a fast releasing profile. Because minocycline is more hydrophilic than rifampin, minocycline releases much faster. For the layered film designs, the release profile and initial burst rate of rifampin and minocycline are tuned and well-controlled through the different designs.

This result shows that by knowing the releasing behaviour of each drug in the different designs, the releasing profile of a drug mixture can be tuned to provide a desired releasing profile. This can be clearly seen from FIG. 6, which shows a significant improvement from literature data where rifampin always has a lower initial burst and slower releasing profile than the other hydrophilic counterpart (in this case minocycline).

Example 12

The zone-of-inhibition (ZOI) for the film was determined according to the Kirby-Bauer method. The study chose to test Escherisia Coli (*E. coli*) and *S.aureus*, S.epidermidisas demonstration. *E. coli* has the highest minimum inhibitory concentration (MIC) among the other bacteria that are commonly found in humans. The MIC of *E. coli* is 20 times higher than *S.aureus, S. epidermidis*, MRSA, *S. capitis* etc.

*E. coli* were inoculated into Lysogeny broth (LB broth) from a stock solution and incubated at 37° C. and then evenly spread over the entirety of an agar plate by a disposable spreader. A 15 mm diameter film was firmly pressed into the center of an agar plate and incubated at 37° C. Pieces were transferred to other fresh agar plates using sterile forceps every 24 hr. The diameter of the ZOI was measured and recorded every day.

TABLE 2

ZOI of layer-by-layer composite film with minocycline and rifampicin.

|  | E. Coli | S. epidermidis | S. aureus |
|---|---|---|---|
| Day 1/mm | 30.0 | 47.3 | 37.3 |
| Day 2/mm | 25.8 | 41.0 | 37.0 |
| Day 3/mm | 23.8 | 39.0 | 36.3 |
| Day 4/mm | 21.5 | 42.0 | 33.3 |
| Day 5/mm | 18.3 | 34.0 | 31.3 |
| Day 6/mm | 16.4 | 34.0 | 27.5 |
| Day 7/mm | 15.8 | 33.8 | 26.8 |
| Day 8/mm | No Zone | 32.4 | 26.3 |
| Day 9/mm |  | 31.0 | 26.8 |
| Day 10/mm |  | 29.9 | 25.8 |
| Day 11/mm |  | 28.7 | 25.0 |
| Day 12/mm |  | 26.5 | 24.5 |
| Day 13/mm |  | 25.0 | 21.0 |
| Day 14/mm |  | 23.9 | 20.3 |

Example 13

The elasticity and fit of the socket was tested using different socket sizes and CIED sizes. A good fit is when the CIED could be easily inserted into the socket, and does not fall out when overturned and held by the socket.

| Socket | CIED Size* | | | Seal to Seal | |
|---|---|---|---|---|---|
| Width (mm) | Width (mm) | Depth (mm) | Stretch Width for Insertion (mm) | length after Insertion | Fit |
| 50 | 43 | 8 | 80 | 51 | Yes |
| 50 | 48 | 7.5 | 80 | 55.5 | Yes |
| 50 | 53 | 7.5 | 85 | 60.5 | Yes |
| 50 | 58 | 7.5 | 85 | 65.5 | Yes |
| 60 | 51 | 15 | 85 | 66 | Yes |
| 60 | 60 | 15 | 90 | 75 | Yes |
| 60 | 75 | 9.9 | 90 | 84.9 | Yes |

*A CIED size is an addition of the width and depth, taking into consideration the volume of space it occupies. As such, the width of the socket is smaller than the size of the CIED (width and depth).

The invention claimed is:

1. A method for manufacturing an implantable film including an upper film layer, an intermediate film layer, and a lower film layer, the method comprising:
   forming the intermediate film layer by:
      combining poly(lactide-co-glycolide) (PLGA), a releasing agent, and an active agent in a solvent, and evaporating the solvent to form the intermediate film layer, wherein the active agent constitutes from 40 wt % to 80 wt % of the intermediate film layer;
   forming the upper film layer on an upper surface of the intermediate film layer by dip coating, wherein the upper film layer includes PLGA and is configured to control release of the active agent from the intermediate film layer; and
   forming the lower film layer on a lower surface of the intermediate film layer by dip coating, wherein the lower film layer includes PLGA and is configured to control release of the active agent from the intermediate film layer.

2. The method of claim 1, wherein the active agent comprises an anesthetic.

3. The method of claim 1, wherein the releasing agent comprises a polysorbate.

4. The method of claim 1, wherein the releasing agent comprises polyethylene glycol.

5. The method of claim 1, further comprising forming one or more holes in the implantable film.

6. The method of claim 5, wherein the one or more holes are configured to enhance release of the active agent when the implantable film is implanted at a surgical site.

7. The method of claim 5, wherein the one or more holes are circular holes.

8. The method of claim 5, wherein the one or more holes each have a diameter within a range from 0.1 mm to 0.5 mm.

9. The method of claim 1, wherein, when implanted at a surgical site, the implantable film is configured to release the active agent at the surgical site over a period of 14 days.

10. The method of claim 1, wherein, when implanted at a surgical site, at least 10 wt % of the active agent is released within 24 hours of implantation.

11. The method of claim 1, wherein the implantable film has a thickness within a range from 500 μm to 2000 μm.

12. The method of claim 1, further comprising compressing the intermediate film layer.

13. The method of claim 1, wherein the releasing agent is configured to enhance release of the active agent from the intermediate film layer.

14. A method for treating a subject, the method comprising:
   implanting a multilayer film at a surgical site in the subject, the multilayer film including an upper film layer, an intermediate film layer, and a lower film layer, wherein the multilayer film is prepared by:

combining poly(lactide-co-glycolide) (PLGA), a releasing agent, and an active agent in a solvent, evaporating the solvent to form the intermediate film layer, wherein the active agent constitutes from 40 wt % to 80 wt % of the intermediate film layer, forming the upper layer on an upper surface of the intermediate layer by dip coating, wherein the upper film layer includes PLGA and is configured to control release of the active agent from the intermediate film layer, and forming the lower film layer on a lower surface of the intermediate film layer by dip coating, wherein the lower film layer includes PLGA and is configured to control release of the active agent from the intermediate film layer.

15. The method of claim 12, further comprising releasing the active agent from the multilayer film over a period of 14 days.

16. The method of claim 12, wherein the active agent comprises an anesthetic.

17. The method of claim 12, wherein the releasing agent comprises a polysorbate or polyethylene glycol.

18. The method of claim 12, wherein the multilayer film comprises one or more holes configured to enhance release of the active agent when the multilayer film is implanted at the surgical site.

19. The method of claim 18, wherein the one or more holes are circular holes.

20. The method of claim 18, wherein the one or more holes each have a diameter within a range from 0.1 mm to 0.5 mm.

* * * * *

UNITED STATES PATENT AND TRADEMARK OFFICE
CERTIFICATE OF CORRECTION

PATENT NO. : 11,964,076 B2
APPLICATION NO. : 17/305851
DATED : April 23, 2024
INVENTOR(S) : Wang et al.

It is certified that error appears in the above-identified patent and that said Letters Patent is hereby corrected as shown below:

On the Title Page

Item (56), in Column 2, under "Other Publications", Line 4, delete "Ionic" and insert -- Ionic --, therefor.

In the Claims

In Column 31, in Claim 15, Line 16, delete "claim 12," and insert -- claim 14, --, therefor.

In Column 31, in Claim 16, Line 19, delete "claim 12," and insert -- claim 14, --, therefor.

In Column 31, in Claim 17, Line 21, delete "claim 12," and insert -- claim 14, --, therefor.

In Column 31, in Claim 18, Line 23, delete "claim 12," and insert -- claim 14, --, therefor.

Signed and Sealed this
Eleventh Day of June, 2024

Katherine Kelly Vidal
*Director of the United States Patent and Trademark Office*